(12) United States Patent
Toti et al.

(10) Patent No.: US 6,553,993 B2
(45) Date of Patent: Apr. 29, 2003

(54) ENDOTRACHEAL TUBE WITH TIP DIRECTIONAL CONTROL AND POSITION PRESERVING MECHANISM

(75) Inventors: Andrew J. Toti, Modesto, CA (US); Michael H. Wong, Irvine, CA (US); Jay Kotin, Irvine, CA (US)

(73) Assignee: Merlyn Associates, Inc., Irvine, CA (US)

( * ) Notice: Subject to any disclaimer, the term of this patent is extended or adjusted under 35 U.S.C. 154(b) by 0 days.

(21) Appl. No.: 09/994,238

(22) Filed: Nov. 27, 2001

(65) Prior Publication Data

US 2002/0043266 A1 Apr. 18, 2002

Related U.S. Application Data

(63) Continuation-in-part of application No. 09/405,750, filed on Sep. 27, 1999, now Pat. No. 6,321,749.

(51) Int. Cl.[7] .............................................. A61M 16/00
(52) U.S. Cl. ............................ 128/207.14; 128/200.26
(58) Field of Search .................... 128/207.14, 207.15, 128/207.18, 200.24, 200.26; 604/95.01–95.05; 600/139; 606/108

(56) References Cited

U.S. PATENT DOCUMENTS

| | | | |
|---|---|---|---|
| 2,458,305 A | 1/1949 | Sanders | |
| 2,541,402 A | 2/1951 | Caine | |
| 3,460,541 A | 8/1969 | Doherty | |
| 3,470,876 A | 10/1969 | Barchilon | |
| 4,148,307 A * | 4/1979 | Utsugi | 600/115 |
| 4,150,676 A * | 4/1979 | Jackson | 128/207.15 |
| 4,329,983 A | 5/1982 | Fletcher | |
| 4,353,358 A | 10/1982 | Emerson | |
| 4,589,410 A * | 5/1986 | Miller | 128/207.15 |
| 4,685,457 A | 8/1987 | Donenfeld | |
| 4,911,148 A | 3/1990 | Sosnowski et al. | |
| 5,231,989 A | 8/1993 | Middleman et al. | |
| 5,255,668 A | 10/1993 | Umeda | |
| 5,259,377 A | 11/1993 | Schroeder | |
| 5,304,131 A | 4/1994 | Paskar | |
| 5,306,245 A | 4/1994 | Heaven | |
| 5,448,989 A | 9/1995 | Heckele | |
| 5,480,382 A * | 1/1996 | Hammerslag et al. | 600/585 |
| 5,489,270 A * | 2/1996 | van Erp | 600/585 |
| 5,520,644 A * | 5/1996 | Imran | 338/128 |
| 5,643,221 A | 7/1997 | Bullard | |
| 5,772,578 A | 6/1998 | Heimberger et al. | |
| 5,791,338 A * | 8/1998 | Merchant et al. | 128/200.26 |
| 5,803,080 A * | 9/1998 | Freitag | 128/200.26 |
| 5,860,914 A * | 1/1999 | Chiba et al. | 600/139 |
| 6,055,984 A * | 5/2000 | Brain | 128/207.14 |
| 6,206,824 B1 * | 3/2001 | Ohara et al. | 600/139 |
| 6,321,749 B1 * | 11/2001 | Toti et al. | 128/200.26 |

FOREIGN PATENT DOCUMENTS

| | | |
|---|---|---|
| EP | 0 422 887 A2 | 4/1991 |
| EP | 0422887 A2 * | 4/1991 |

* cited by examiner

Primary Examiner—Aaron J. Lewis
Assistant Examiner—Teena Mitchell
(74) Attorney, Agent, or Firm—Leonard Tachner

(57) ABSTRACT

An endotracheal tube which facilitates rapid intubation of the trachea, especially in situations where anatomical variation creates difficult intubating conditions, includes a portion that can be bent during placement to control the position of the distal end of the tube. The distal end of the endotracheal tube may be selectively curled or bent by a mechanism or fluid passage accessible from the proximal end of the endotracheal tube. The endotracheal tube provides for manipulation of the insertion end without occluding the lumen of the tube, to facilitate placement of the tube.

41 Claims, 20 Drawing Sheets

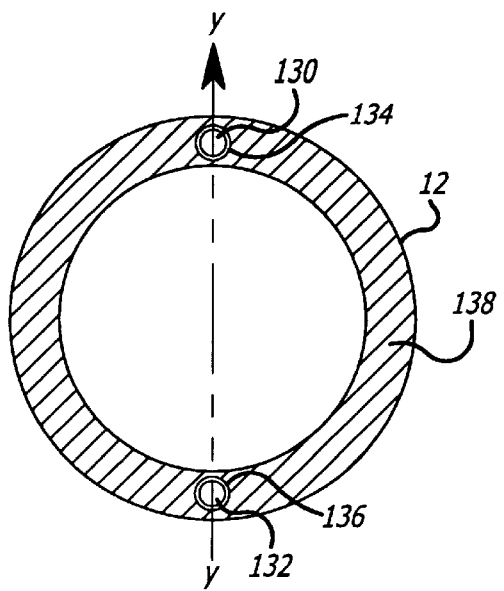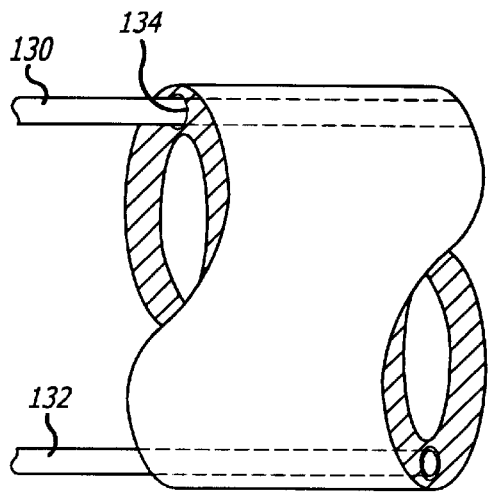
FIG. 19          FIG. 19A
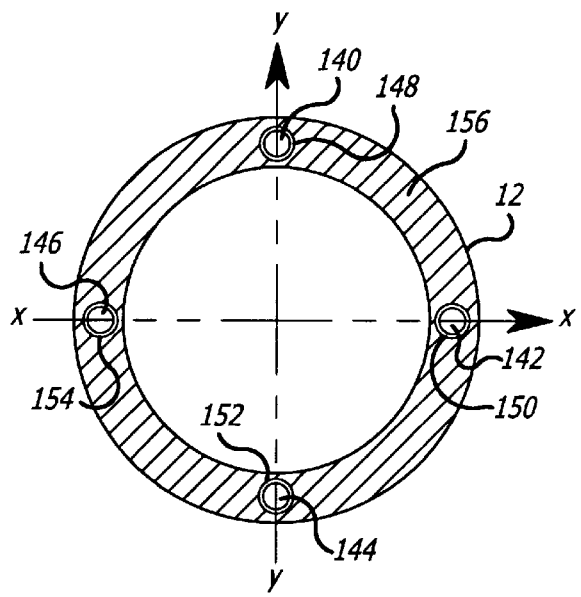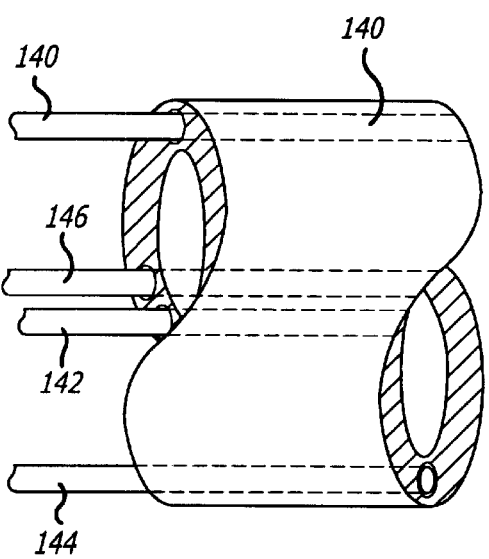
FIG. 20          FIG. 20A

ENDOTRACHEAL TUBE WITH TIP DIRECTIONAL CONTROL AND POSITION PRESERVING MECHANISM

This application is a continuation-in-part of U.S. application Ser. No. 09/405,750, filed Sep. 27, 1999, U.S. Pat. No. 6,321,749 which is hereby incorporated by reference in its entirety into the present disclosure.

BACKGROUND OF THE INVENTION

1. Field of the Invention

This invention generally relates to endotracheal tubes, and more particularly, to endotracheal tubes having a bendable portion designed to facilitate intubation of difficult airways (tracheal inlet opening) caused by anatomical variation, trauma and the like.

2. General Background and State of the Art

An endotracheal tube generally comprises a cylindrical tube used as an air passage to administer oxygen and anesthetic gases directly to the patient. The cylindrical tube terminates in an open distal end configured for insertion into the trachea and has an opposite open proximal end configured to be coupled to a gas source. The endotracheal tube typically has an inflatable cuff on the exterior of the cylindrical tube for forming a seal with the interior walls of the trachea. (See U.S. Pat. No. 3,460,541 to Doherty). The cuff functions to occlude the trachea which protects the trachea and lungs against aspiration of foreign substances. In particular, food, foreign bodies or digestive system contents are prevented from entering the lungs. The endotracheal tube is used primarily in surgery, but is also frequently used in emergency rooms and emergency in-the-field situations.

In surgical procedures requiring general anesthesia, the patient is rendered unconscious by administration of anesthetic agents including drugs and/or gases. The patient is also given a muscle relaxant/paralyzing agent to minimize the patient's gagging response to the insertion of the endotracheal tube. A laryngoscope is placed in the mouth of the patient. The blade portion of the laryngoscope is used to push the tongue laterally and the intubating practitioner applies a lifting force to the laryngoscope handle in order to visualize the anatomical structures of the mouth and airway. A specific target area of the tracheal tube is the glottis, which is the opening between the vocal cords and the inlet to the trachea. The distal end of the endotracheal tube is inserted into the glottis and the inflatable cuff (balloon) is filled with air to create an airtight seal between the cuff walls and the interior walls of the trachea. This airtight seal allows for delivery of the oxygen and anesthetic gases with positive pressure directly to the air passages below the tip and the balloon.

Patient anatomies differ greatly and fall into specific categories that are grouped according to potential difficulty of tube insertion. In a patient with an anterior glottis or target orifice (the vocal cords and opening positioned high in the patient's neck and to the front of the neck), placing the insertion end of the endotracheal tube through the opening can be extremely difficult, and can lead to serious injury and even death from lack of oxygen. Although careful evaluation by the anesthesiologist or healthcare practitioner may suggest difficulty, the condition is usually undetectable until the orifice and vocal cords are visualized with a laryngoscope and blade apparatus. When this occurs, the practitioner must remove the laryngoscope, and the insert a metal or plastic stylette (semi-rigid wire) into the lumen of the endotracheal tube, bend the tube and stylette into an appropriate configuration to aid in placing the insertion tip in its proper location and to act as a placement guide. A small bend, resembling the shape of a hockey stick, is made in the stylette and the end of the endotracheal tube, while the main body of the tube remains unchanged. Once this is accomplished, another attempt is made by the practitioner to visualize the vocal cords and inlet. The bent shape of the insertion tip improves the chances of passing the tip through the tracheal orifice. An example of early endotracheal tube including a stylette for curvature is described in U.S. Pat. No. 2,458,305 to Sanders.

Although this method of using a stylette to bend the insertion end of the endotracheal is widely used, it has many shortcomings. The steps of bending the tube in the correct configuration, subsequent visualizing the path of insertion, and then removing the stylette from the lumen of the endotracheal tube wastes valuable time in completing the intubation procedure. Time is of the utmost importance in an unconscious patient who is not breathing, particularly where the patient may have a full stomach with an increased chance for aspiration of foreign substance.

Also, the use of a stylette is usually employed after an initial attempt has been made with the laryngoscope in place. Further, because of there intended use stylettes must be semi-rigid, capable of being easily bent and, once bent, and shape retaining. This inherent characteristic places a patient at risk of an injury from the stylette to the airway with potential for bleeding in the airway as well. In the past, puncture of soft tissue and vocal cord damage has been attributed to the use of stylettes.

None of the prior devices have succeeded in the elimination of the use of a stylette to properly configure an endotracheal tube and successfully intubate a patient.

Many devices have been designed to assist in the placement of the tracheal tube in the target orifice. For example, laryngoscopes have been developed to aid in insertion. However, these devices do not provide any mechanism for controlling the curvature of the insertion end of the endotracheal tube itself.

U.S. Pat. No. 4,589,410 to Miller, U.S. Pat. No. 4,150,676 to Jackson and U.S. Pat. No. 4,685,457 to Donenfeld each show an endotracheal tube with at least one pull cord in the wall along a portion of the length of the tube. Applying tension on the cord causes the tube at a position proximal to the balloon to curl, apparently due to the compressibility of the material of construction. However, the tip of the tube does not bend, the bending being distributed along the whole length of the pull cord. These devices do not employ a hinge or spring-type mechanism or altered tube wall, nor do they use a locking device. As a result, these prior devices do not allow selected movement at the tip of the tube. In these prior devices, the body of the tube is moved by a pulley mechanism which bends a considerable portion of the tube, thus creating problems due movement of the tube within the mouth.

Other devices employing tube bending mechanism include U.S. Pat. No. 5,255,668 to Umeda is directed to a bendable endoscope used for broncoscopy which includes a bendable distal portion spaced between two coils in the wall of the tube, the bendable portion is caused to bend by pulling on a wire in the wall of the tube. U.S. Pat. No. 4,911,148 to Sosnowski et al. is directed to small diameter (diameter of 0.15 mm or less) endoscopes which have a series of radial notches spaced along the length of the tube and a pull wire through the notched wall. Pulling on the wire causes the tube to bend along the portion containing the notches, which in turn causes the tip to deflect. U.S. Pat. No. 5,304,131 to Paskar shows an arterial or venous catheter with an area of weakness along one side of the catheter. The weakness is the result of gaps cut through the wall of the catheter. Bending of the weakened portion is provided by a wire running through the wall on the side of the gaps. To aid in returning the weakened portion to its original straight orientation that portion may be surrounded by a spring and, to seal the weakened portion, a jacket can cover the spring and the weakened portion.

U.S. Pat. No. 4,353,358 to Emerson is directed to a flexible sigmoidoscope which has notches and a pull wire similar to Sosnowski et al. Other flexible tipped endoscopes and catheters with hinged portions and a pull wire are also shown in U.S. Pat. No. 5,772,578 to Heimberger, et al. and U.S. Pat. No. 5,448,989 to Heckele. U.S. Pat. No. 5,306,245 to Heaven shows a bendable tubular device which includes a cutaway wall opposite a flexible stainless steel hinge with a pull wire in the tube wall opposite to the hinge. At least the cut-out portion is covered by an outer plastic material. This plastic cover may also cover the pull wire, as well as the full length of the tube. A balloon may be added distal to the bendable portion. These devices do not include an occlusion balloon such as is required on an endotracheal tube. While Heaven includes a balloon, it is distal to the bendable portion and used for cholangiographic purposes and is not intended to seal a trachea.

None of these devices in the preceding two paragraphs are intended to operate in the manner of an endotracheal tube. They do not incorporate features of the invention, such that a portion of the tube near the insertion tip articulates, while the main portion of the tube remains in its original preset shape.

While there have been various changes, improvements and developments in endotracheal tubes, there still remains a need for a device that can bend only at the tip and has a mechanism to temporarily lock the position in place. Such an endotracheal tube would facilitate one-handed manipulation of the tube while the other hand is free to manipulate other devices, such as a laryngoscope. Also, this should be accomplished without having to compromise the lumen of the tube.

INVENTION SUMMARY

The endotracheal tube of the present invention has a distal end configured to be inserted into a human trachea that can be manipulated, without the use of a stylette or other guiding device, while the tip of the tube is approaching the glottis. The main tube body remains in its original configuration, while allowing the distal end to be independently curved or bent and maintained in a desired position during placement of the endotracheal tube. The lumen of the endotracheal tube remains unoccluded during the curving of the distal tip so as not to block the patient's airways. Creating the desired distal tip curvature is accomplished by the use of various designs, all contemplated as within the scope of the invention, in combination with one or more mechanisms for manipulating the distal end of the tube. In accordance with one specific, exemplary embodiment of the invention, these include:

1) locating a spring between distal tip and main tube body;
2) using ultrasound, heat, solvent treatment or like methods, to modify the molecular structure or composition of the polymer forming the portion of the tube to be bent so as to increase flexibility of that portion;
3) using of a polymer baffle between the distal tip and main tube body;
4) surrounding the portion to be bent by a polymer spring; or
5) providing a thin, notched or cutout area between distal tip and main body tube with or without the support spring.

All of the above mechanisms may be applied to the outside of the endotracheal tube, incorporated in the wall of the tube, or inserted within the lumen of the tube. The endotracheal tube of the present invention also contemplates a control mechanism for causing movement of the tip and temporary locking of the bend which is imposed on the distal end tube. This can be accomplished by the use of a friction lock mechanism, a single axis lock, a sliding trigger with catch, a detent system, or a similar locking device which cooperates with a pull wire. This locked position permits the practitioner to have at least one hand free to manipulate other devices. In its preferred operation, one hand holds the endotracheal tube while the laryngoscope is operated with the other hand. After the curved end of the tube is inserted in its desired position, the trigger mechanism can be easily released and the tube allowed to assume its original configuration. An endotracheal tube incorporating features of the invention preferably does not have an occluded tube lumen, allows the practitioner to have superior tip control, and allows rapid achievement of airway control.

BRIEF DESCRIPTION OF THE DRAWINGS

The following invention will become better understood with reference to the specification, appended claims, and accompanying drawings, where:

FIG. 19 and 19A comprise, respectively, a cross section view and a side view of a portion of an endotracheal tube in accordance with an eight embodiment;

FIGS. 20 and 20A comprise, respectively, a cross section view and a side view of a portion of an endotracheal tube in accordance with a ninth embodiment;

DETAILED DESCRIPTION OF THE PREFERRED EMBODIMENTS

Figure 15:
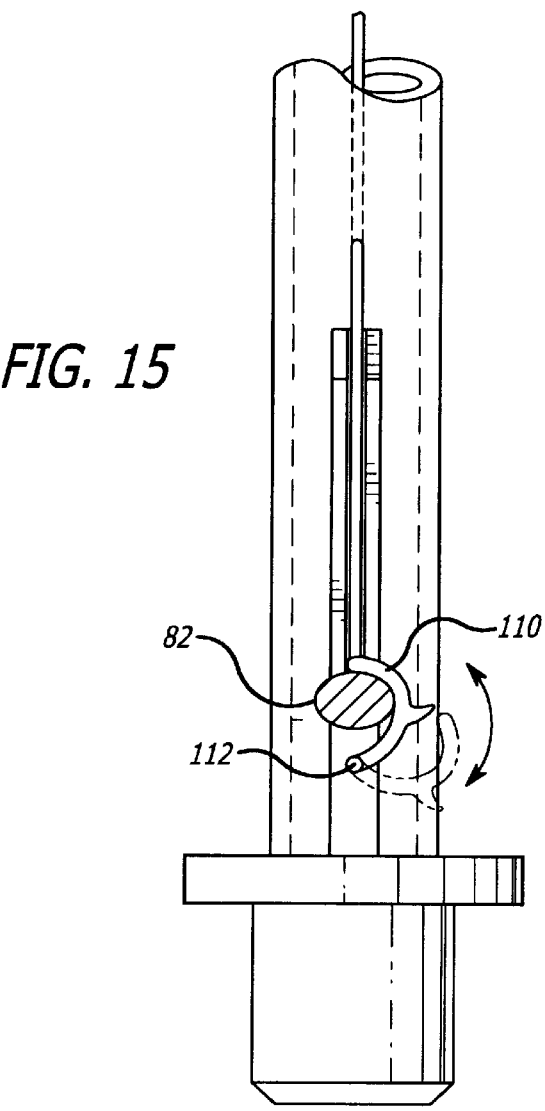
FIG. 15 is a top view of the proximal end of the endotracheal tube shown in FIG. 14.

A first embodiment of a tracheal tube 10, alternatively referred to as an endotracheal tube, incorporating features of the invention is shown in FIGS. 15. Tracheal tube 10, has a hollow tubular body 12 with an inflatable balloon 14, also referred to as a cuff, mounted on the external surface of tubular body 12 near the distal end 16 thereof. Connected to the space between tubular body 12 and cuff 14, or the inflatable portion of the cuff in a multi-walled balloon, is a conduit 18 which runs from the proximal end 20 of tubular body 12 to the distal end 16 of tubular body 12. Conduit 18 is used to inflate balloon 14 to a desired occluding diameter once tubular body 12 is placed in its desired location in the air passage of a patient. Conduit 18 is typically a small diameter tube 22 which runs through a passageway 24 within wall 26 of tubular body 12, or along the inner or outer surface of wall 26. Alternatively, passageway 24 in wall 26 can constitute conduit 18 with the small diameter tubular body 12 sealed into the proximal end of passageway 24. On the proximal end of the small diameter tube 22 is a valve 28, which acts to retain the inflation air in balloon 14 and, typically, a pilot balloon 30 which inflates when cuff 14 meets resistance from the trachea to further inflation. While the drawings show a cuff 14 with a diameter greater than the outer diameter of tubular body 12, the Figures all show cuff 14 and pilot balloon 30 in a deflated configuration, the cuff and balloon being further enlarged when inflated.

Figures 1, 1A:
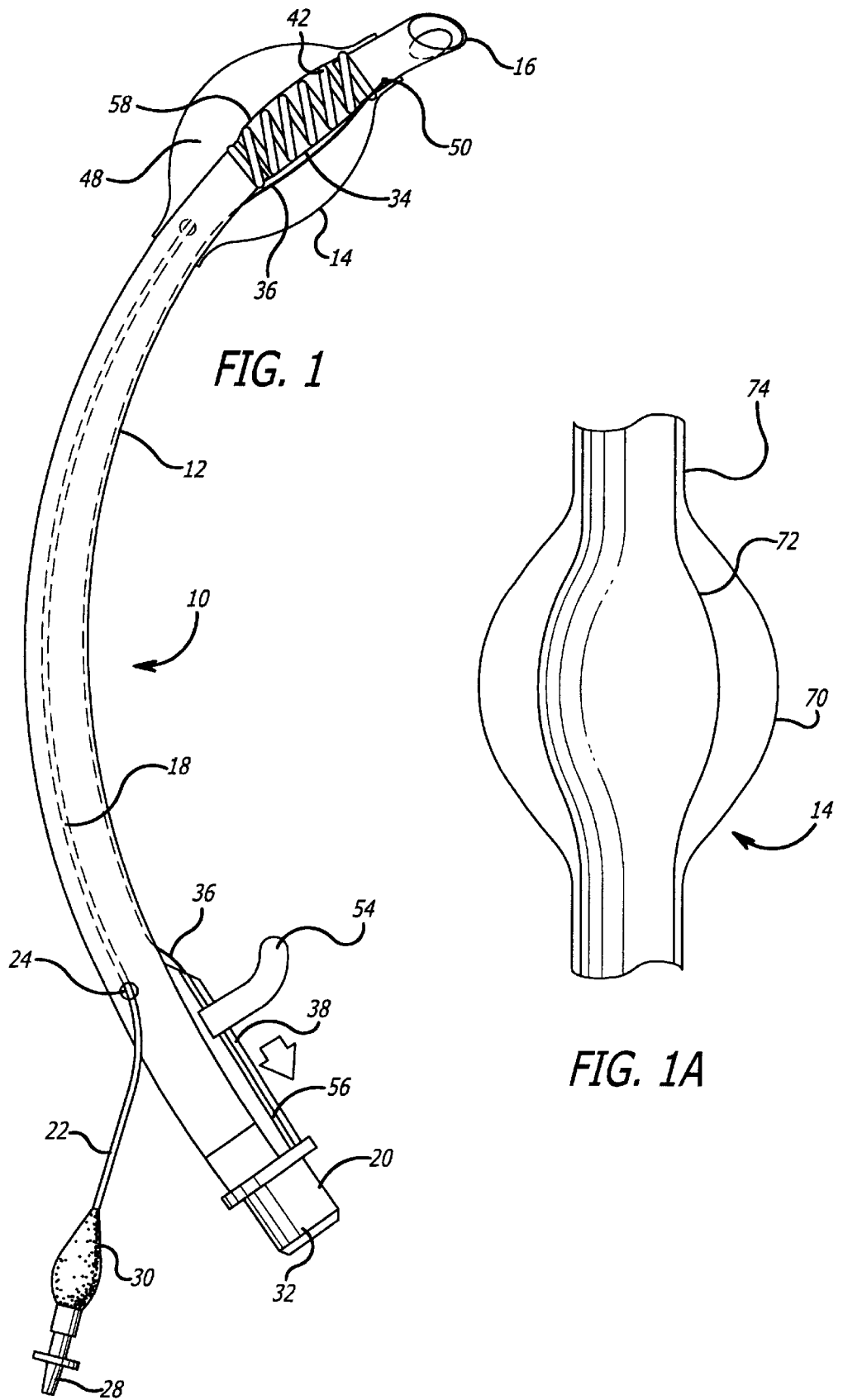
FIG. 1 is a partial cutaway view of an endotracheal tube incorporating features of the invention.
FIG. 1A is an enlarged cutaway view of the balloon shown in FIG. 1.

On proximal end 20 of tubular body 12 is an adapter 32 for connecting tracheal tube 10 to a source of air, oxygen, or gaseous anesthetic mixture, such as a respirator or wall mounted air supply (not shown). Distal end 16 of tubular body 12 is open to allow gas fed into the tube to flow without obstruction into the patient's air ways. In FIG. 1, distal end 16 shows an alternative tip design comprising two side openings and a protected tip end so that a smooth leading surface is presented to the tissue of the air passage to minimize trauma to the tissue during placement of the tracheal tube 10.

Figure 6:
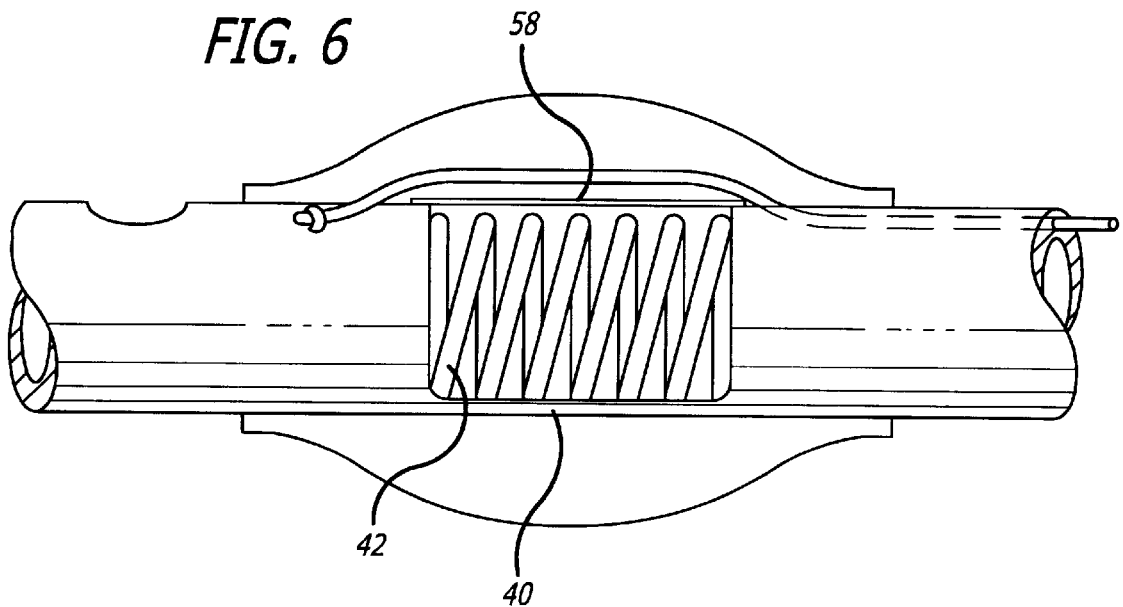
FIG. 6 is an enlarged, partial cutaway view of the distal portion of a second embodiment of an endotracheal tube incorporating features of the invention showing the bendable portion of the device.
Figure 7:
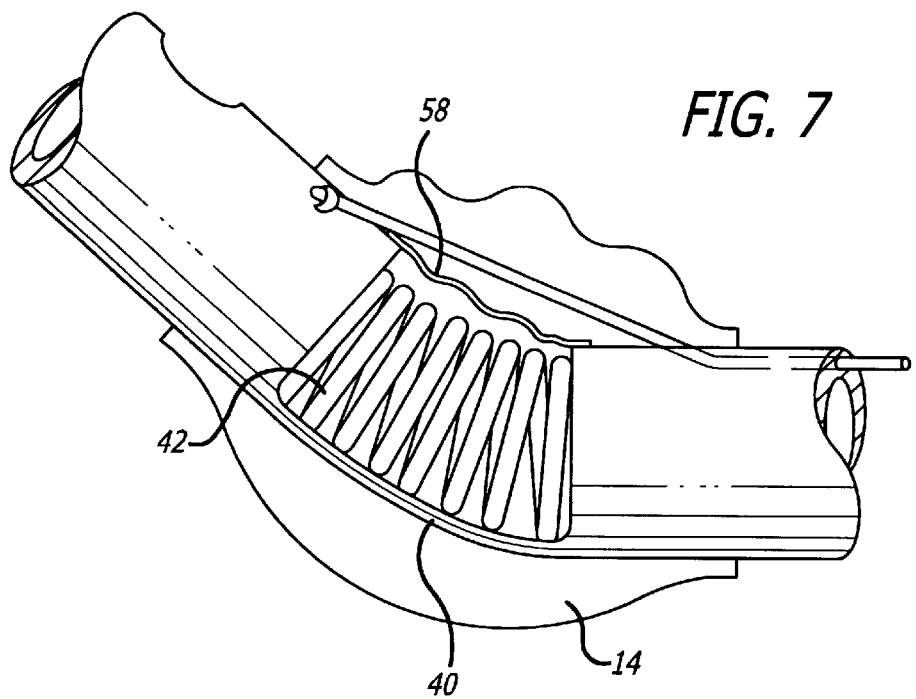
FIG. 7 is an enlarged, partial cutaway view of the distal portion of the endotracheal tube of FIG. 6 showing the bendable portion of the device in its bent configuration.

Tracheal tube 10 includes a flexible portion 34 in the wall of tubular body 12 covered by cuff 14, a cable 36 extending from proximal end 20 to distal end 16 of tubular body 12, and a control mechanism 38 attached to proximal end of the cable 36. In a first embodiment, flexible portion 34 is created by removing some or all of wall 26 in the area under cuff 14. If a portion of the wall is retained, retained portion 40 is along the side of tubular body 12 opposite where cable 36 is located as shown in the embodiment of FIGS. 6–7. Retained portion 40 bends acting as a hinge. In the first embodiment, to provide support and integrity for flexible portion 34 and to bring the bent tube back to its initial shape once the deforming force is released, a coil spring 42 is located within flexible portion 34 of tubular body 12.

Where a portion of tube wall 26 is removed, a self-contained cuff 14, such as shown in FIG. 1A, is provided so that the air space within the cuff is completely isolated from the gas stream flowing through the tracheal tube 10. The self-contained cuff 14 then has an outer membrane 70 which is expanded against the trachea and an inner membrane 72 facing the open area in the tube wall. The end portions 74 are provided to seal cuff 14 to the outside surface of tubular body 12. Conduit 18 is used to inflate balloon 14.

Figure 4:
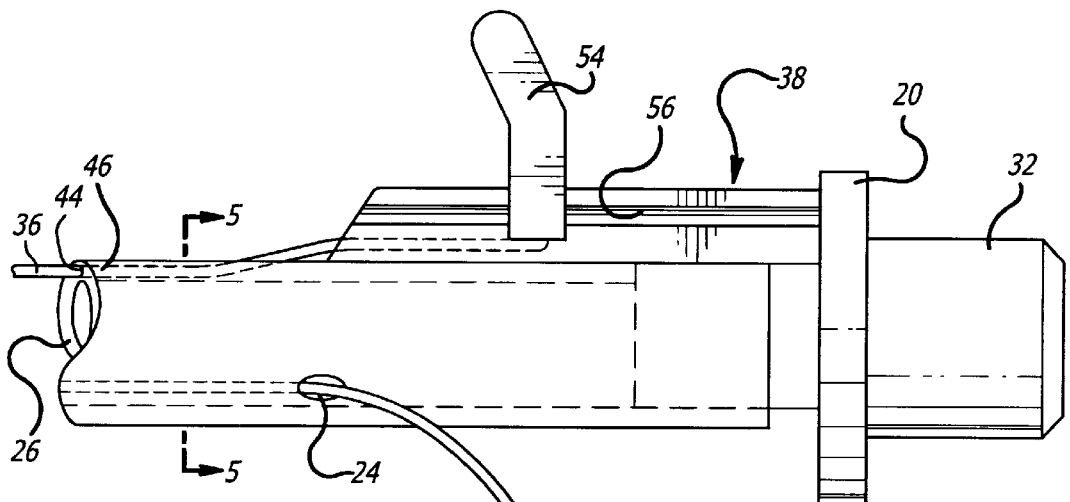
FIG. 4 is an enlarged, partial cutaway view of the endotracheal tube of FIG. 2 showing the control portion of the device in the tip retracted position.
Figure 4:
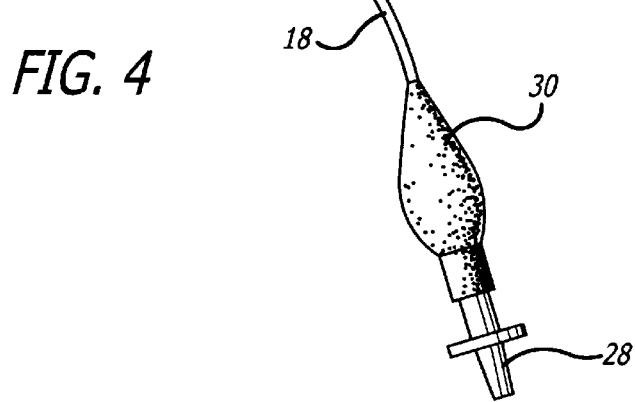

Cable 36 is threaded through a hole 44 in wall 26 of tubular body 12 near proximal end 20 of tubular body 12, as best shown in FIG. 4. Cable 36 may run through the lumen of tubular body 12 or through a second passageway 46 in the wall of tubular body 12 to the vicinity of cuff 14 where it exits through wall 26 into space 48 enclosed by cuff 14. The distal end 50 of cable 36 is then attached to wall 26 of the tubular body 12 at a point 52 more distal from the exit point, but still within the space 48. Attachment may be by adhesives, clips, rings or other attachment devices or techniques known to those skilled in the art. Cable 36 may be formed from various materials. For example, it may be a thin wire, such as piano wire or surgical stainless wire, a plastic filament such as nylon monofilament, multifilament braided structures or sutures, or any other variety of materials typically used as sutures or tensioning cords.

Figure 2:
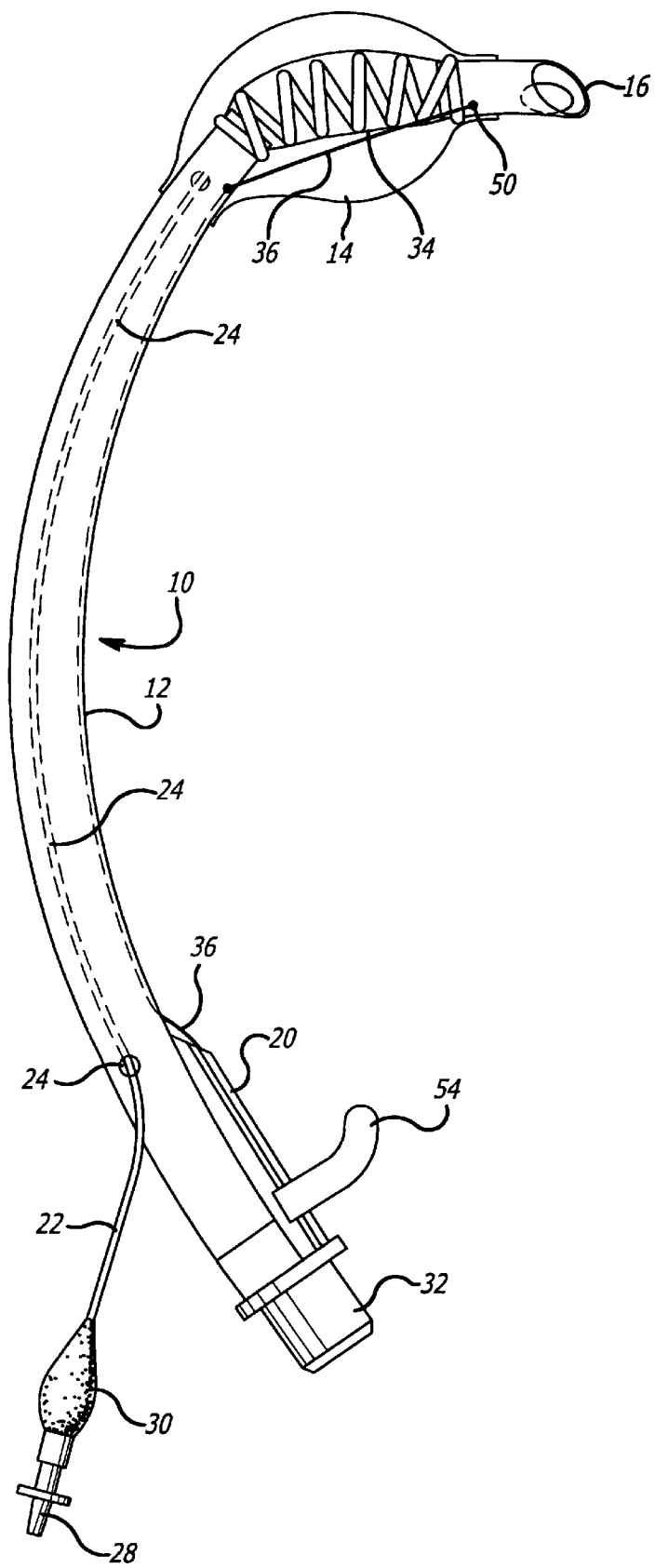
FIG. 2 is a partial cutaway view of an endotracheal tube of FIG. 1 with the tip bending function activated.
Figure 3:
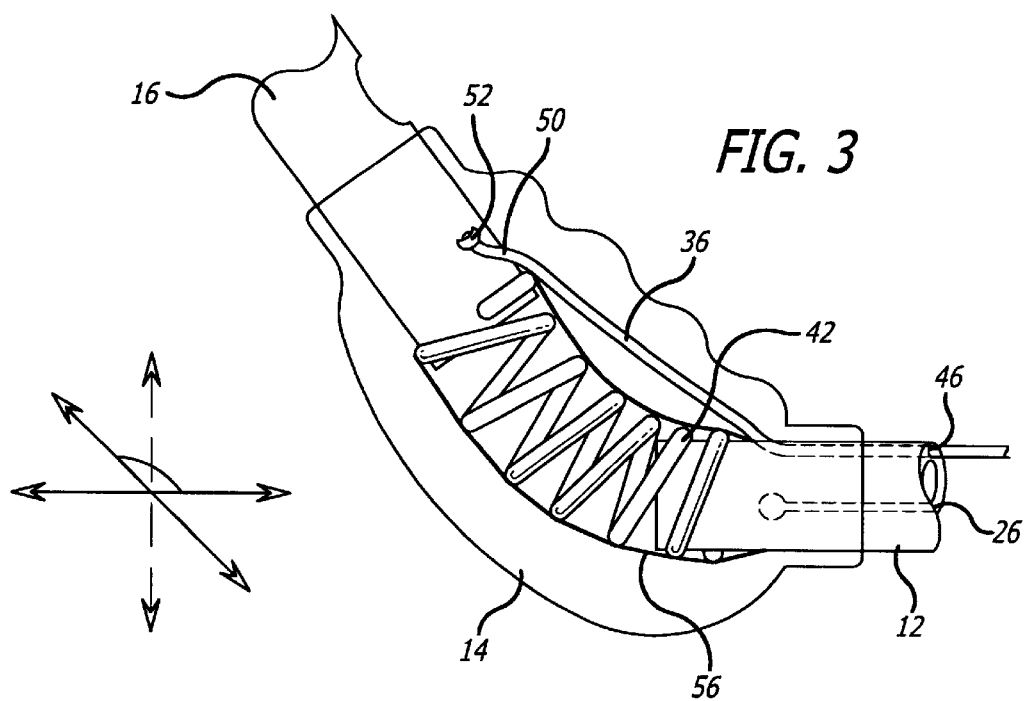
FIG. 3 is an enlarged, partial cutaway view of the distal portion of the endotracheal tube of FIG. 2 showing the bent portion of the device.
Figure 5:
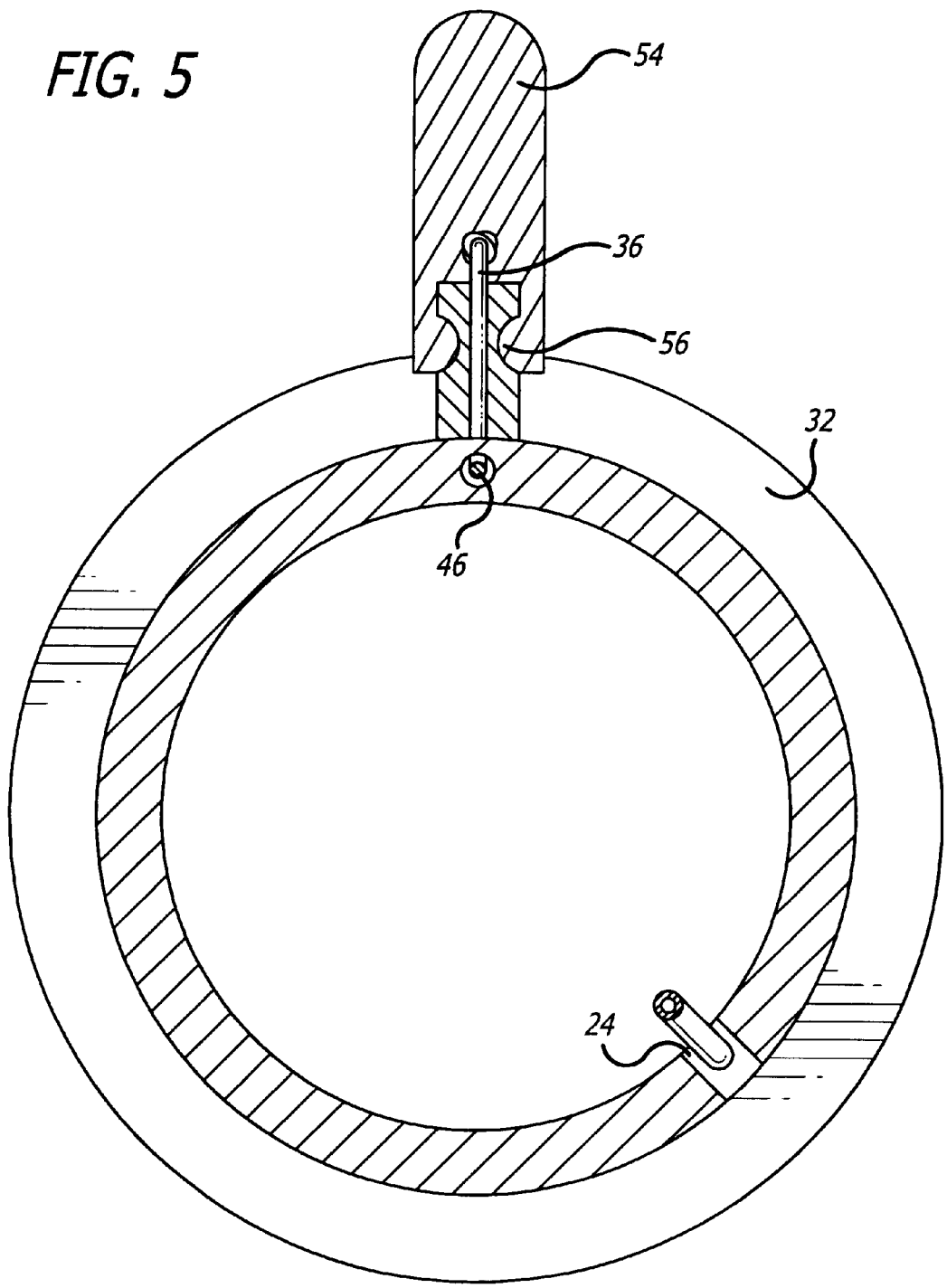
FIG. 5 is an end view taking along line 5—5 of FIG. 4 showing the proximal end of the endotracheal tube.

Mounted on proximal end 20 of tubular body 12 is a handle or trigger 54 movable longitudinally within a slide channel 56 (FIGS. 4 and 5). The proximal end of cable 36 is attached to trigger 54 so that when an operator retracts the trigger 54 in the direction indicated by the arrow in FIG. 1, the pulling force is transmitted to distal point 52 of cable attachment, causing tubular body 12 to bend in the area covered by cuff 14 and spring 42 to flex as shown in FIGS. 2 and 3. When the trigger is released, spring 42 causes tubular body 12 to return to the unbent configuration as shown in FIG. 1. The trigger 54 and slide channel 56 may be so dimensioned that sufficient friction exists between these elements to retain the trigger 54 in its retracted position.

FIGS. 6 and 7 show a modification of the first embodiment where a stretchable but substantially non-expandable membrane 58 covers flexible portion 34 to separate cable 36 and lumen of tubular body 12 from spring 42 and to prevent gas flowing through tubular body 12 from creating an expanding or pulsatile force on cuff 14. In this instance, the membrane 58 acts as the inner membrane 72 of cuff 14 in FIG. 1A and the cable passes through cuff 14 rather than between balloon inner membrane 72 and spring 42. Otherwise, the modification of FIGS. 6 and 7 functions in the same manner as the first embodiment.

Figure 8:
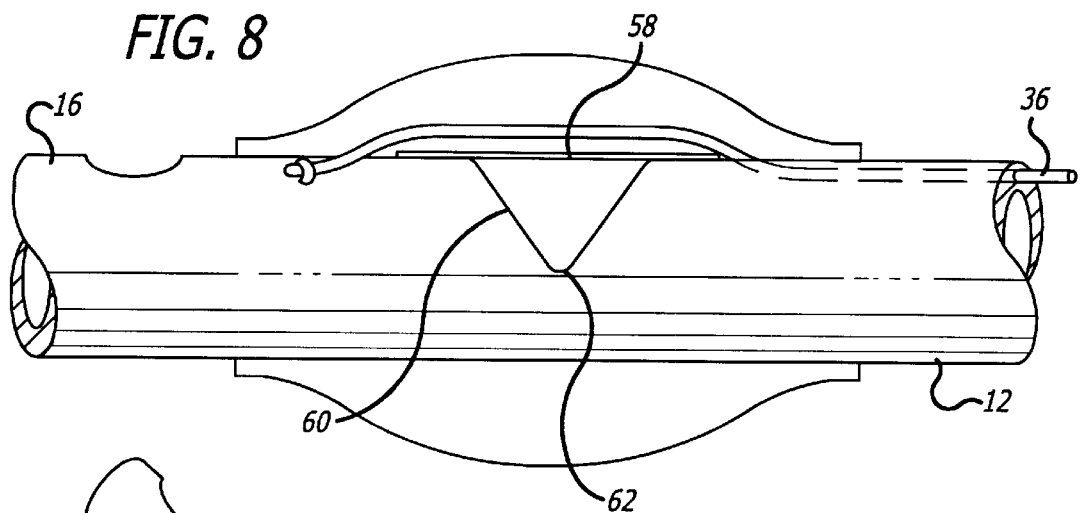
FIG. 8 is an enlarged, partial cutaway view of the distal portion of a third embodiment of an endotracheal tube incorporating features of the invention showing the bendable portion of the device.
Figure 9:
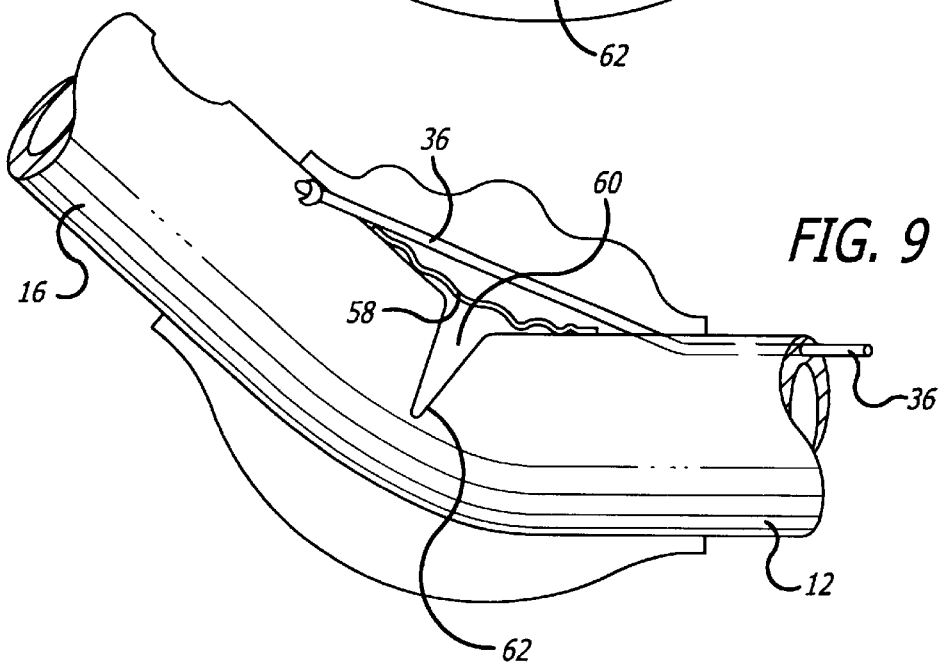
FIG. 9 is an enlarged, partial cutaway view of the distal portion of the endotracheal tube of the FIG. 8 showing the bendable portion of the device in its bent configuration.

FIGS. 8 and 9 show a further embodiment where flexible portion 34 is created by providing one or more notches 60 in wall 26 with bottom 62 of the notch 60 functioning as a hinge. While this embodiment does not show the use of the spring 42, a spring can be used within that portion of the tube for the same purposes as set forth above. A membrane 58 is shown covering the notch 60 and forming the inner membrane 72 of cuff 14.

Figure 11:
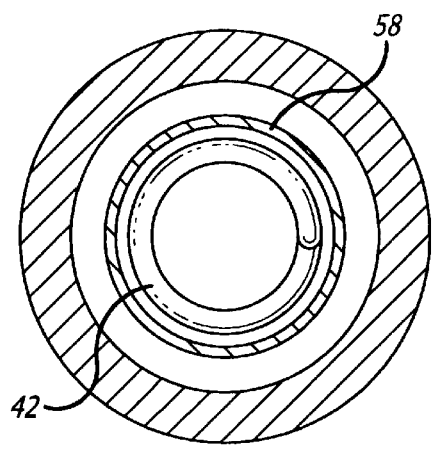
FIG. 11 is a cross sectional view taken along line 11—11 of FIG. 10.
Figure 10:
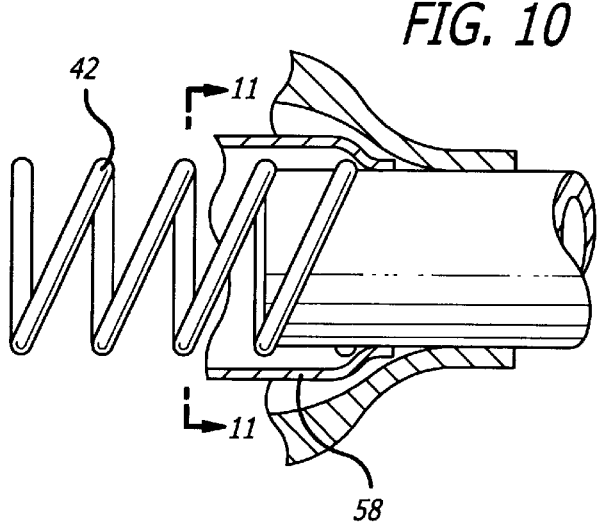
FIG. 10 is an enlarged, partial cutaway view of a fourth embodiment of the distal portion of the endotracheal tube incorporating features of the invention showing the bendable portion of the device.

FIG. 10 shows a cutaway view and FIG. 11 shows an end view of an alternative embodiment of the endotracheal tube of the present invention having a distal end with an inner membrane 58 covering the spring 42.

Figure 12:
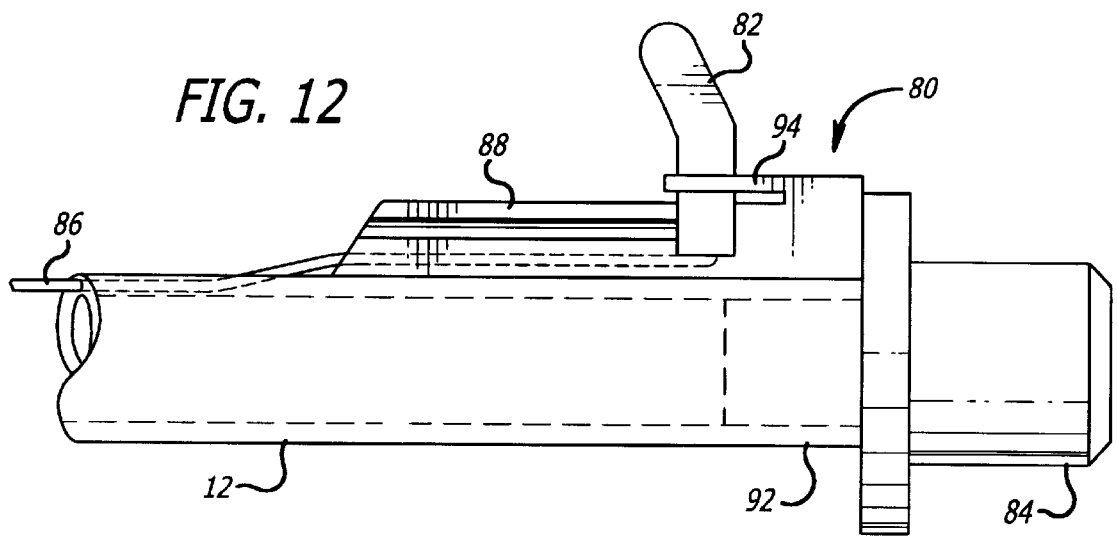
FIG. 12 is a side view of the proximal end of an endotracheal tube in accordance with a fifth embodiment of the invention.
Figure 13:
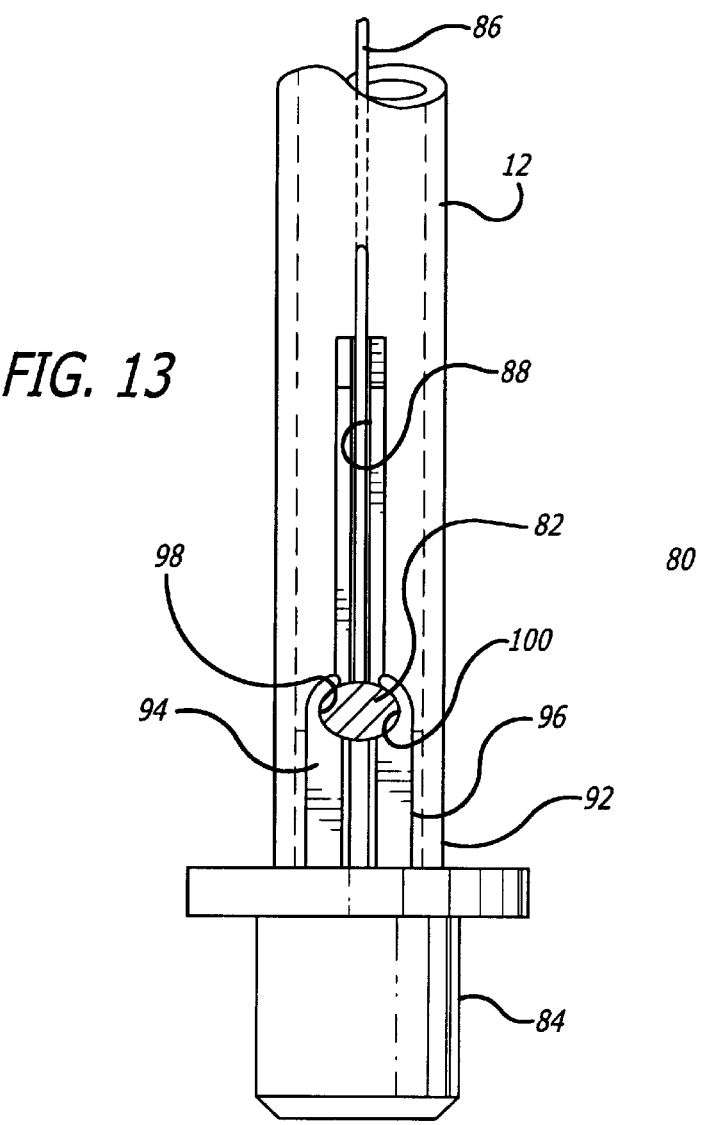
FIG. 13 is a top view of the proximal end of the endotracheal tube shown in FIG. 12.

FIGS. 12 and 13 show a fifth embodiment of the present invention including a mechanism 80 for retaining the handle or trigger 82 in its fully retracted position. The embodiment of FIGS. 12 and 13 includes a universal connector 84 received by the proximal end of the endotracheal tube 12. The handle or trigger is attached to a cable 86 and is movable within a longitudinally extending slide channel 88 to bend or flex the distal end 16 of the endotracheal tube 12 as already explained. Mounted on the proximal end 92 of the tube 12 is a pair of longitudinally extending, flexible retention members 94, 96 having opposed recesses 98, 100 for receiving and retaining the trigger 82 when the trigger is in its fully retracted position, as shown in FIGS. 12 and 13. This retention mechanism allows one-handed manipulation of the trigger as previously described.

Figure 14:
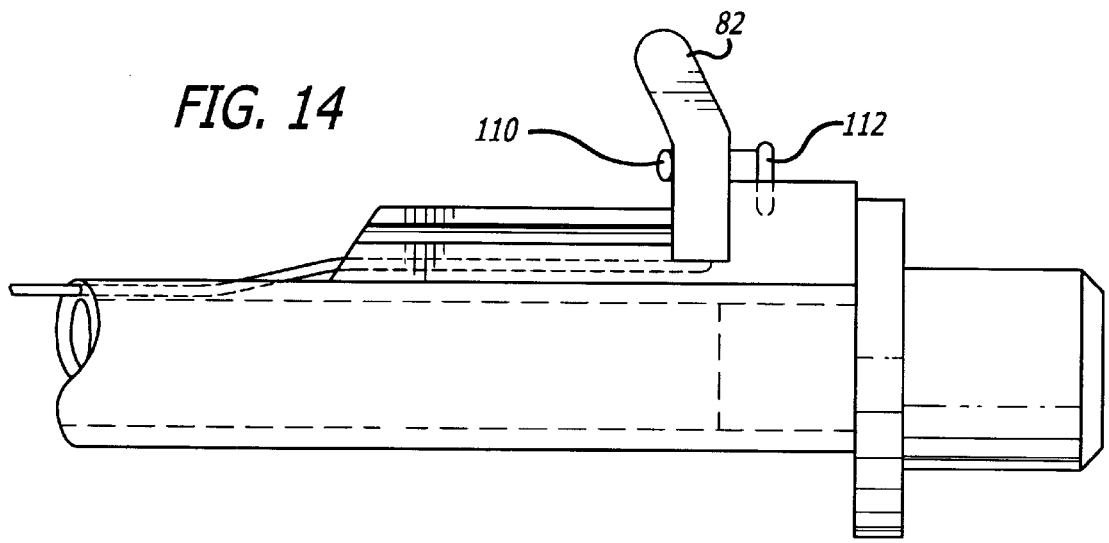
FIG. 14 is a side view of the proximal end of an endotracheal tube in accordance with a sixth embodiment of the invention.

FIGS. 14 and 15 show a sixth embodiment of the invention which includes an alternative retention mechanism for holding the cable trigger 82 in its fully retracted position. In this embodiment, a hook 110 rotatable about a vertical axis 112 is movable between a latched and unlatched position. In the latched position, shown in FIGS. 14 and 15, the trigger 82 is held by the hook 110 in its fully retracted position. The trigger is released when the hook 110 is rotated clockwise, as seen in FIG. 15.

Figure 16:
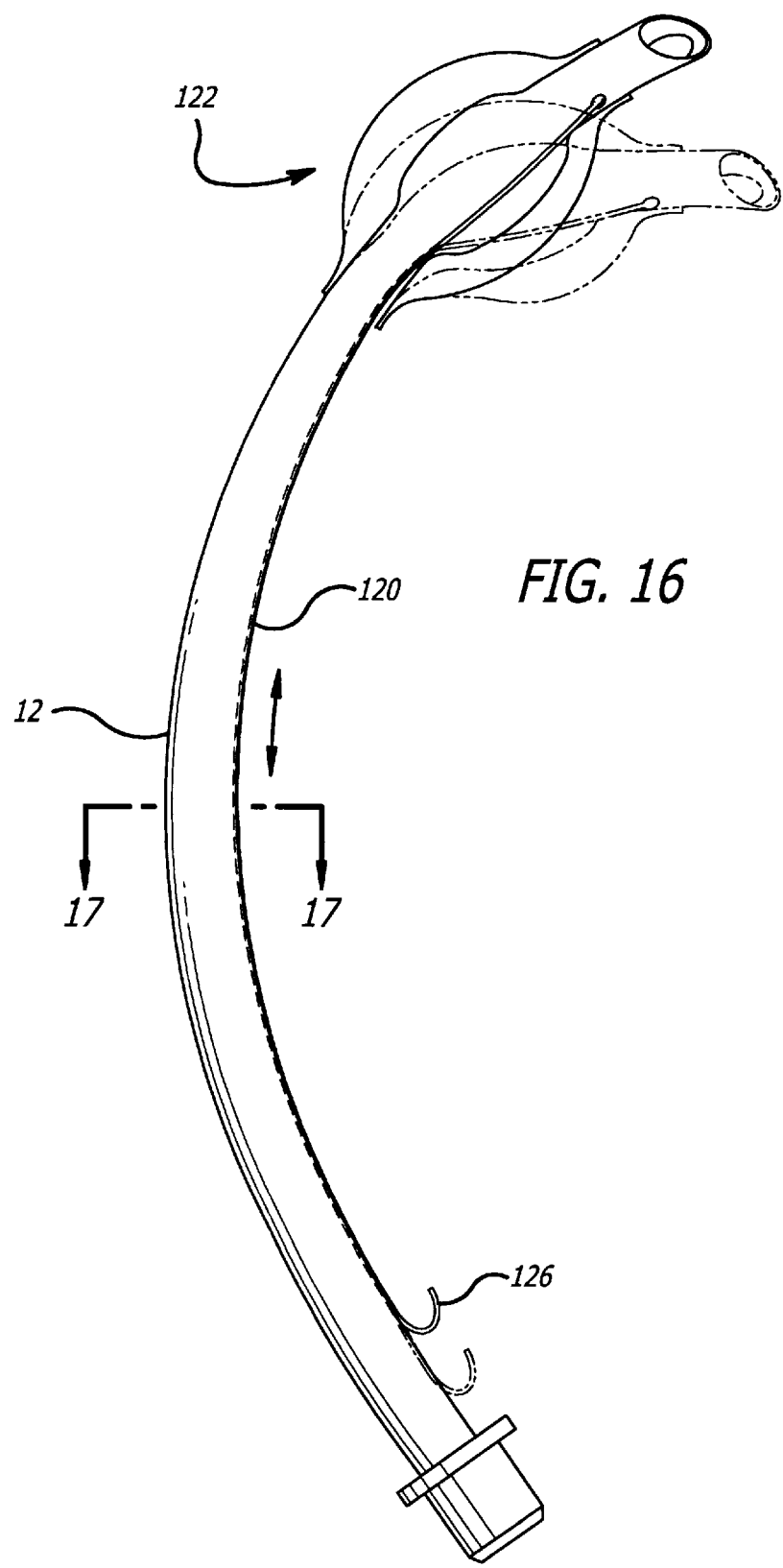
FIG. 16 is a side view of an endotracheal tube in accordance with a seventh embodiment of the invention.
Figure 17:
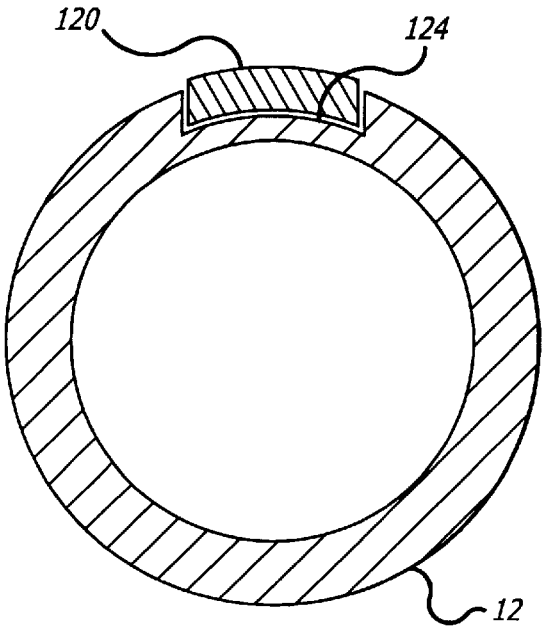
FIG. 17 is a cross section view of the endotracheal tube of FIG. 16 as seen along the line 17—17.
Figure 18:
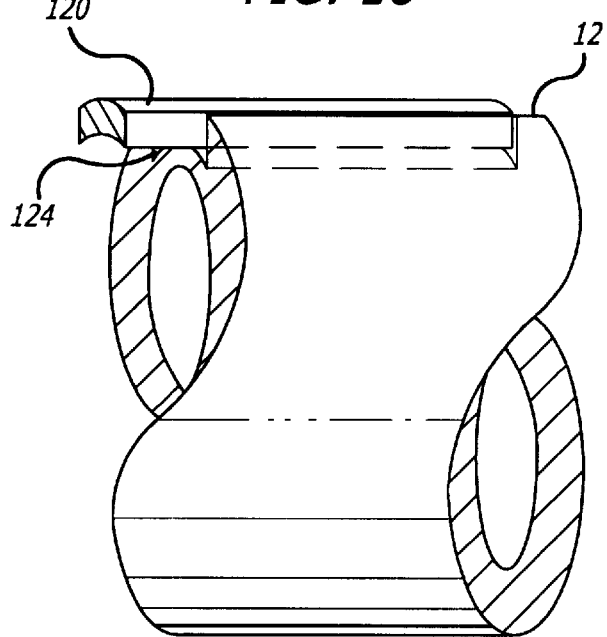
FIG. 18 is side of view of a portion of the endotracheal tube of FIG. 16 showing certain details thereof.

FIGS. 16–18 show a seventh embodiment of the invention which includes a curved, relatively rigid, sliding bar or flattened wire 120 to actuate the flexible distal tip 122. The bar or wire 120 is slidably disposed within a longitudinally extending groove or channel 124 formed in the wall of the tube 12, as best seen in FIGS. 17 and 18. A hook 126 on the proximal end of the bar or wire 120 is used to actuate the distal tip between its bent and unbent configurations.

FIGS. 19 and 19A show an eighth embodiment of the invention in which, instead of a single cable for bending the distal tip, a pair of cables 130,132 disposed within passageways 134, 136 within the wall 138 of the endotracheal tube 12 are used to flex or bend the distal tip in either of two directions along a y-axis shown in FIG. 19. An alternative to this arrangement, providing for even greater versatility, is shown in the ninth embodiment of the invention in FIGS. 20 and 20A. In this case, four cables 140, 142, 144 and 146, disposed within passageways 148, 150, 152 and 154 spaced at 90° intervals within the wall 156 of the endotracheal tube 12 can be used to flex the tip in either direction along an x-axis, a y-axis or anywhere in between, thus providing the greatest degree of options so as to permit more precise control of the direction of the bending of the distal tip.

Figure 21:
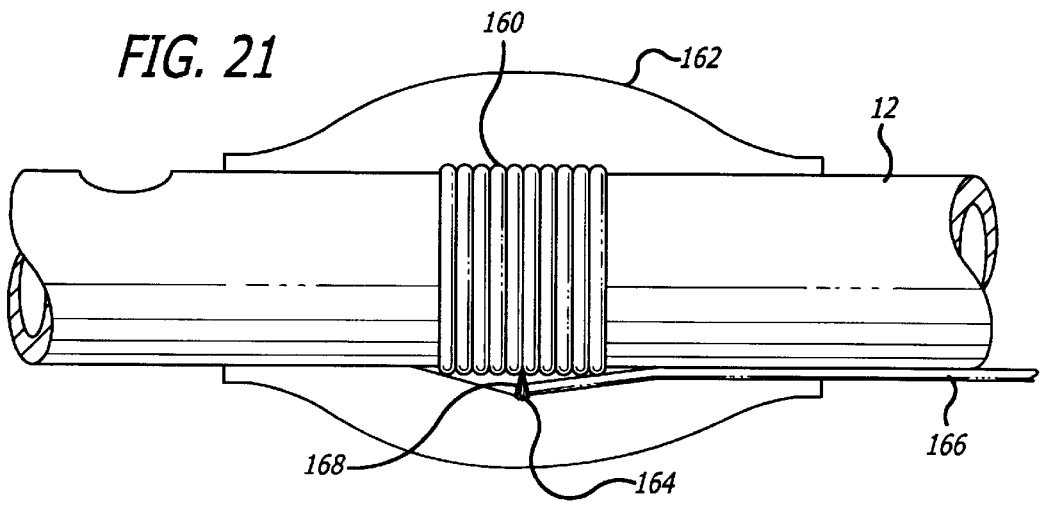
FIGS. 21 and 22 are side views of the proximal end of an endotracheal tube in accordance with a tenth embodiment, showing the proximal end in its unbent and bent configurations, respectively.
Figure 22:
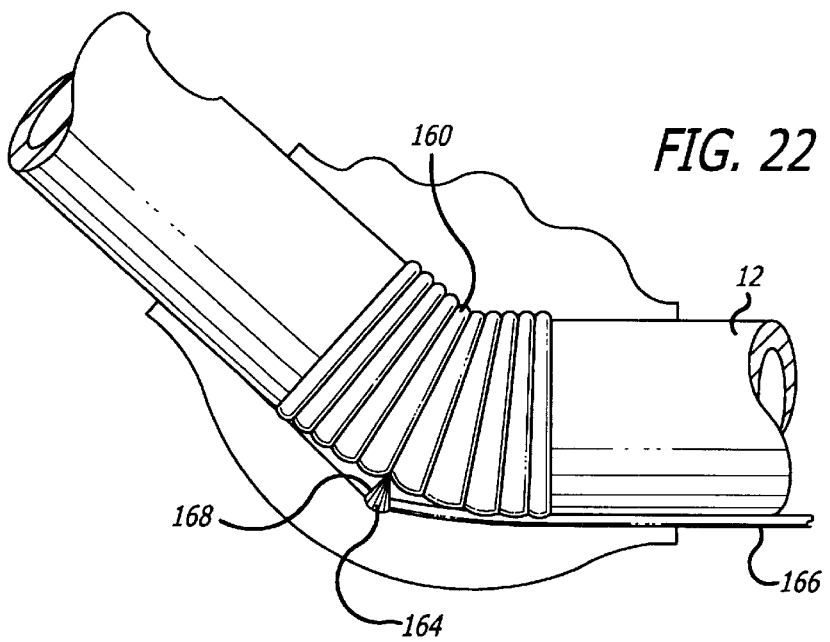
Figure 23:
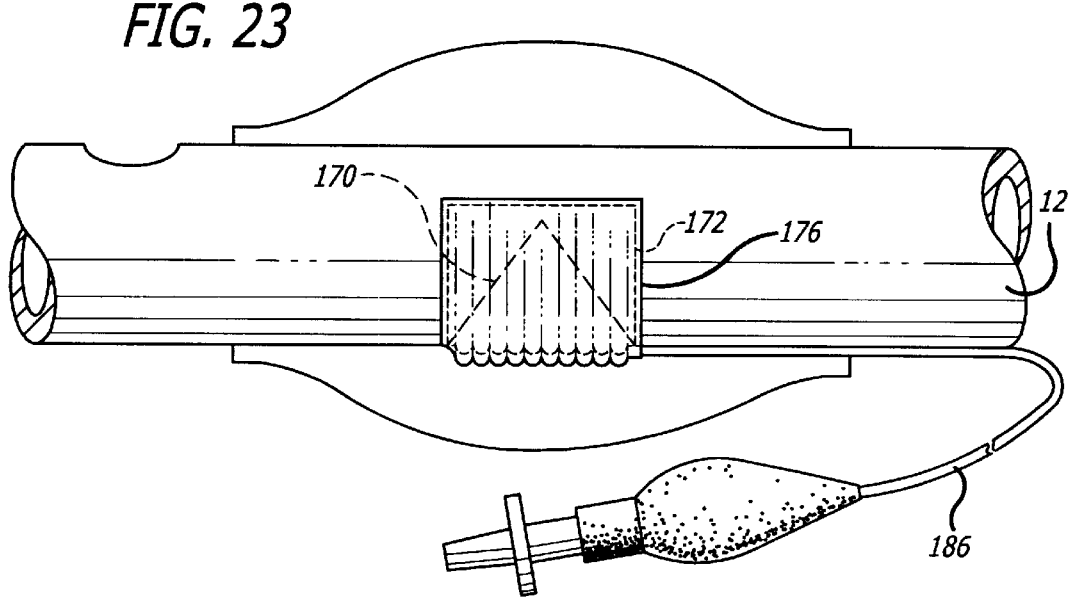
FIGS. 23 and 24 are side views of the proximal end of an endotracheal tube in accordance with an eleventh embodiment of the invention, showing the proximal end in its unbent and bent configurations, respectively.
Figure 24:
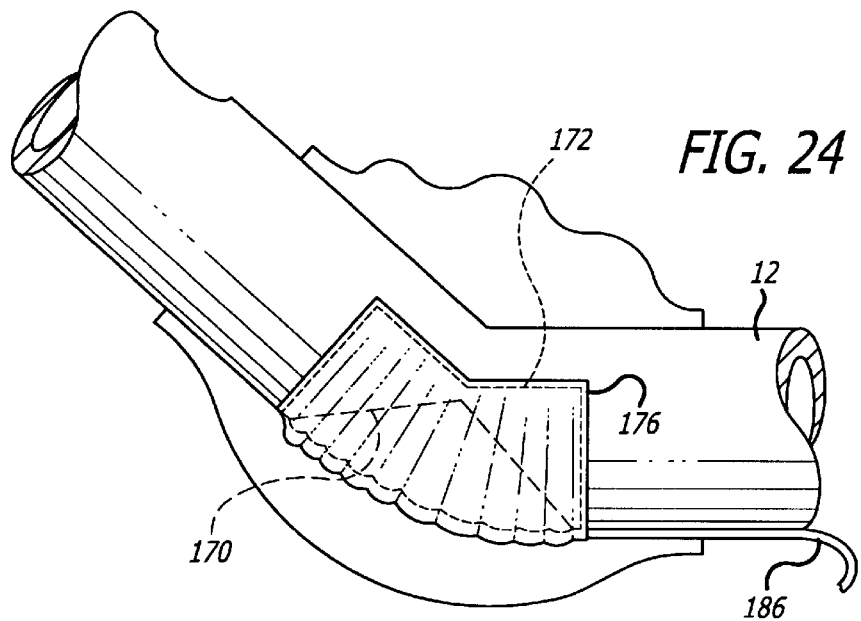

FIGS. 21 and 22 show a tenth embodiment of the invention in which flexibility of the distal tip of the endotracheal tube is provided by a bellows section 160 within the cuff 162. Such a flexible bellows section allows movement of the distal tip in any direction while preserving the airtight integrity of the tube without any additional covering. The embodiment of FIGS. 21 and 22 includes a small baffle chamber 164 disposed along the underside of the bellows section 160 of the distal tip of the endotracheal tube. Air or fluid forced into this chamber by way of a small diameter tube 166 causes expansion of the small baffle chamber 164 against a fixed projection 168 extending from the underside of the bellows section. FIG. 22 shows the distal tip of this embodiment in its flexed or bent configuration upon the introduction of air or other fluid under pressure into the small baffle chamber 164.

Figure 25:
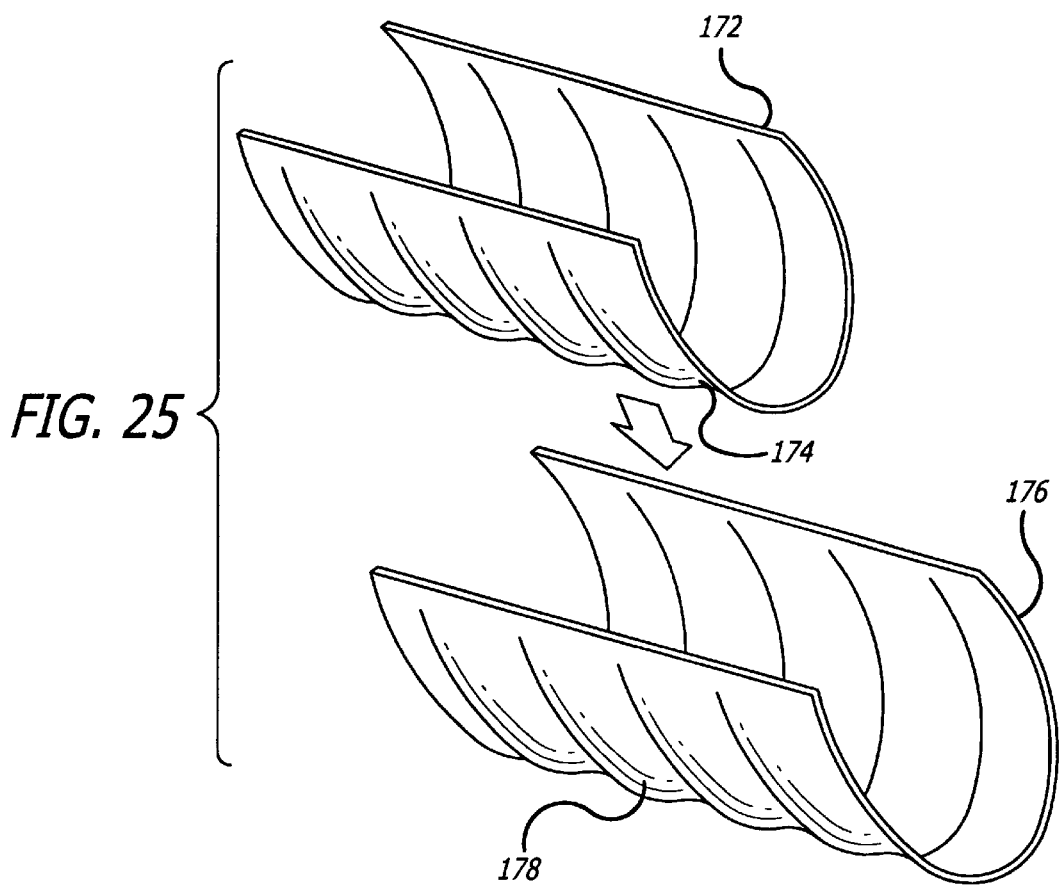
FIG. 25 is a perspective views of a pair of flexible membranes used in the embodiment of FIGS. 23 and 24.
Figure 26:
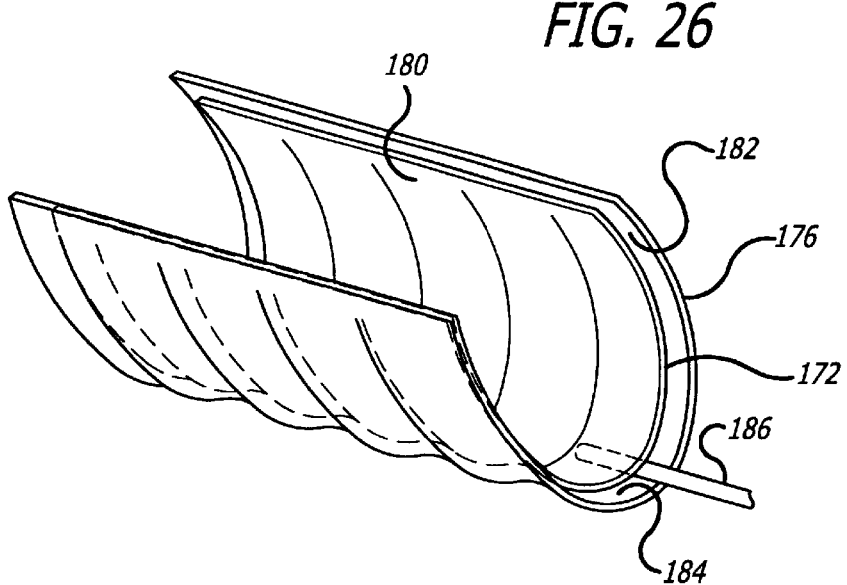
FIG. 26 is a perspective view of the pair of membranes of FIG. 25 showing in their nested or assembled configuration.
Figure 27:
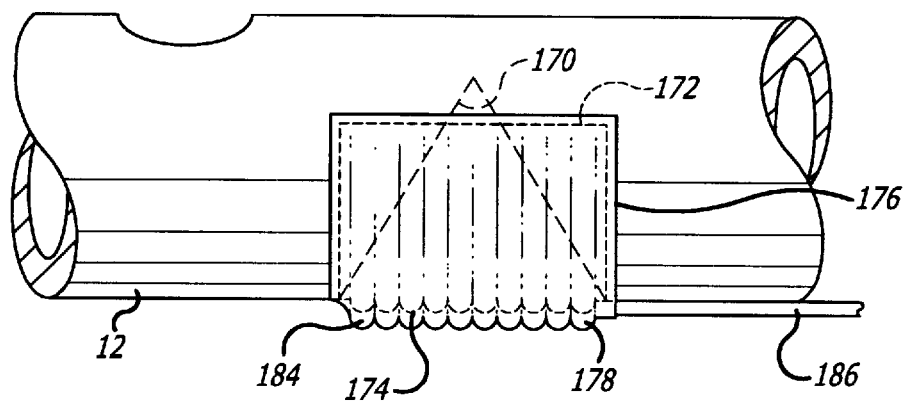
FIGS. 27 and 28 are enlarged side views of the proximal end of the endotracheal tube of FIGS. 23 and 24, respectively.
Figure 28:
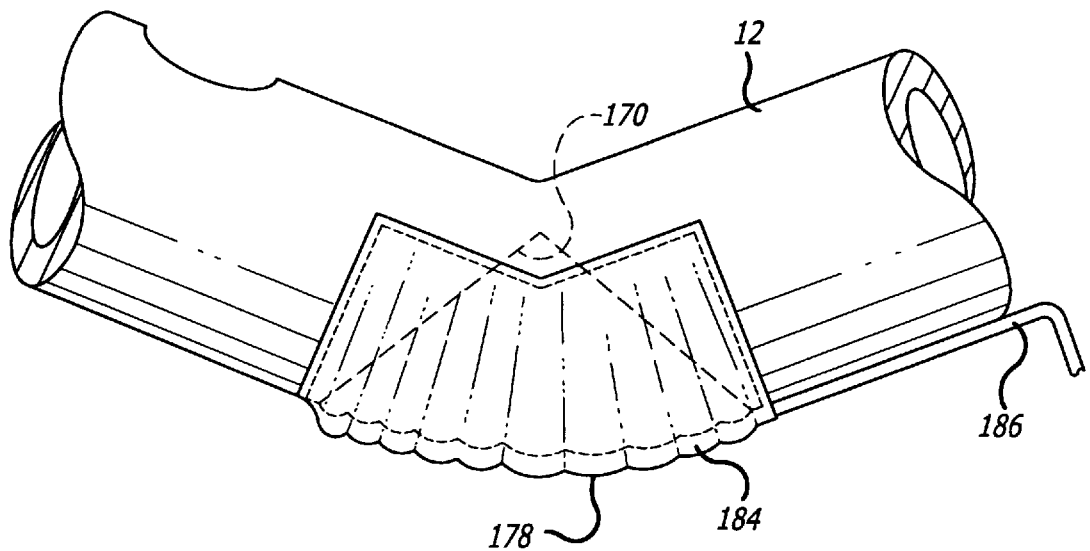

FIG. 23–28 show an eleventh embodiment of the present invention. In this embodiment, flexibility of the distal tip is provided by a V notch 170 formed in the underside of the distal end of the endotracheal tube 12. This V-shaped cutout or notch 170 is covered by a dual membrane, details of which are shown in FIGS. 25 and 26. A first flexible, inner membrane 172 including laterally oriented corrugations 174 is configured to nest within a similar, outer flexible membrane 176 also including laterally disposed corrugations 178. The corrugations allow expansion of the membranes. The membranes are bonded together along their edges 180, 182 so as to define an enclosed space 184 therebetween. Air or fluid under pressure is supplied to this space by means of a small diameter tube 186. FIGS. 27 and 28 show the distal tip of the endotracheal tube of this embodiment in its unflexed or unbent configuration and in its bent or flexed configuration when air or other fluid is forced into the space 184 between the inner and outer membranes.

Figure 29:
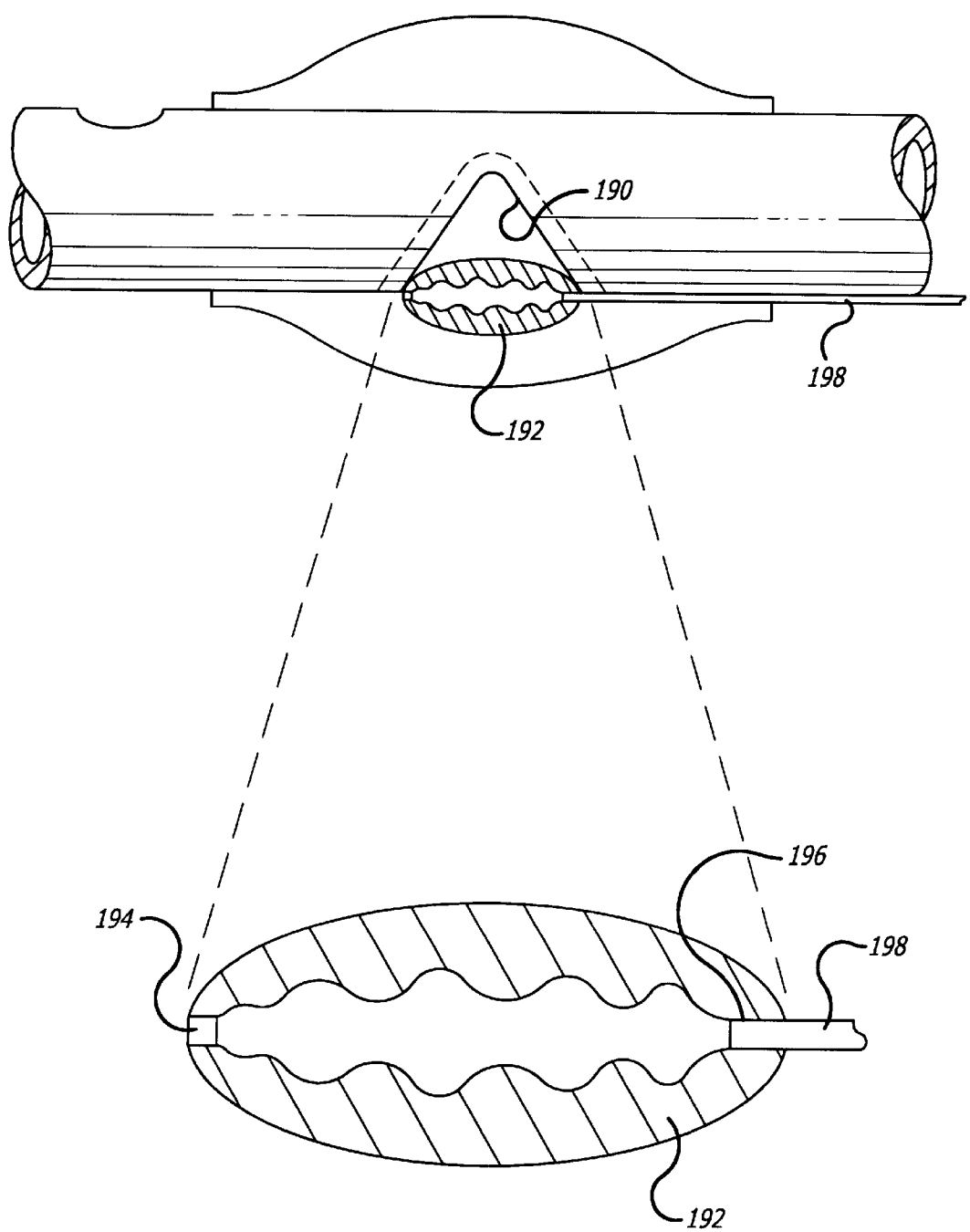
FIG. 29 and 30 are side views of the proximal end of an endotracheal tube in accordance with a twelfth embodiment of the invention, showing the proximal end in its unbent and bent configurations, respectively.
Figure 30:
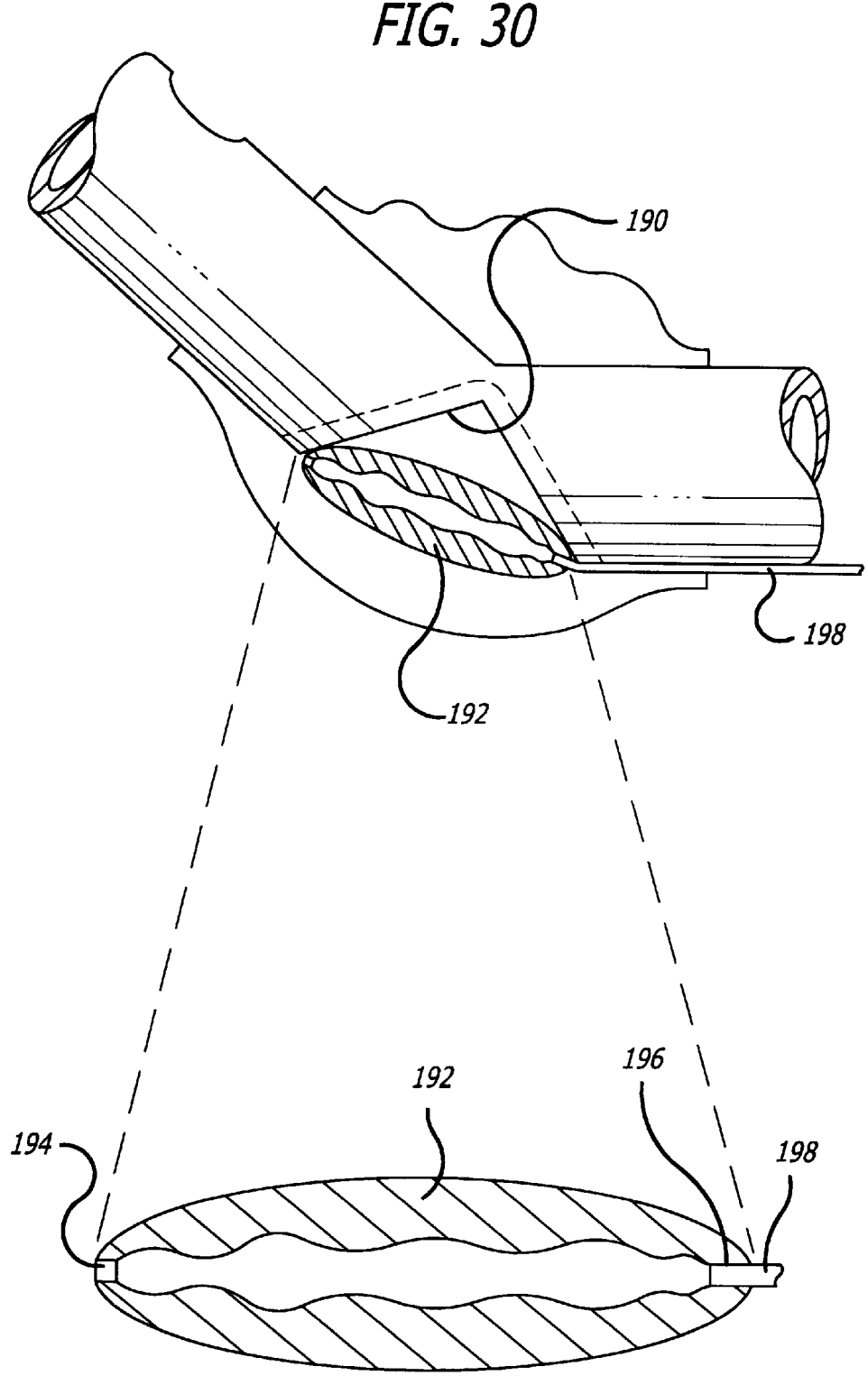

FIGS. 29 and 30 show a twelfth embodiment of the invention comprising an endotracheal tube having a distal end including a cuff, as already described. A V-shaped cutout or notch 190 is formed in the distal end of the endotracheal tube 12 within the confines of the cuff. Inserted into the lower end of the V-shaped notch 190 is an expandable balloon 192 having a distal extremity 194 and a proximal extremity 196. The distal extremity 194 is sealed while the proximal extremity receives the distal end of a small diameter tube 198. The distal end of the tube 198 is bonded or otherwise secured in fluid-tight fashion within the proximal end 196 of the balloon. Air or other fluid forced into the balloon causes expansion thereof and flexing or bending of the distal end of the endotracheal tube, as best seen in FIG. 30.

The embodiments of FIGS. 21–30 show the small diameter tubes 166, 186 and 198 for supplying air or other fluid to the baffle chamber 164, dual membrane 172, 176, and balloon 192. The small diameter tubes are illustrated as co-extruded to the exteriors of the primary tubular bodies. However, the small diameter tubes can also be co-extruded to the interiors of the primary tubular bodies. Alternatively, the small diameter tubes can extend within the passageways in the walls of the primary tubular bodies in a similar fashion to the conduit 18 illustrated in FIG. 1. Also, the passageways in the walls themselves can constitute the air-tight or fluid-tight small diameter tubes in which case the small diameter tubes are sealed into the proximal ends of passageways.

Although the present invention has been described in considerable detail with reference to certain preferred versions and uses thereof, other versions and uses are contemplated by the invention. For example, it is not necessary to purposely provide a flexible portion to the wall nor is it necessary that the distal portion of the cable be placed between the cuff and the tube outer wall. The bending action can be obtained using a standard cuffed endotracheal tube with the cable run through the lumen of the tube or in the wall of the tube. The cable then exits through the wall just proximal of the cuff and is attached to the wall just distal of the cuff (i.e., external to the cuff). Pulling on the cable in the manner described above causes the tube to bend in the region covered by the cuff.

Further, it is not necessary to limit the flexible portion 34 to the cuff area. Any portion of the tube can be caused to bend by providing a cable exiting through the tube wall before the desired bendable section and attaching the cable proximal thereto. Pulling on the cable bends the tube within that portion where the cable is external to the tube.

Other variations contemplated within the general scope of the device described above include other means of creating a flexible portion such as by providing the tubular body a corrugated tube wall or making the distal end portion of the tubular body of a material that is more flexible than the remainder of the tubular body.

In some applications the inflatable cuff is neither needed nor desirable. For example, when used with some children, the endotracheal tube forms a seal with the interior walls of the trachea without use of the inflatable cuff, and elimination of the cuff reduces the thickness of the device for easier insertion and manipulation. Also, the cuffless device of the present embodiment can be used for applications other than as an endotracheal tube, for example, as a cannula for insertion into a human or animal body. for applications other than as an endotracheal tube, for example, as a cannula for insertion into a human or animal body.

Figure 31A:
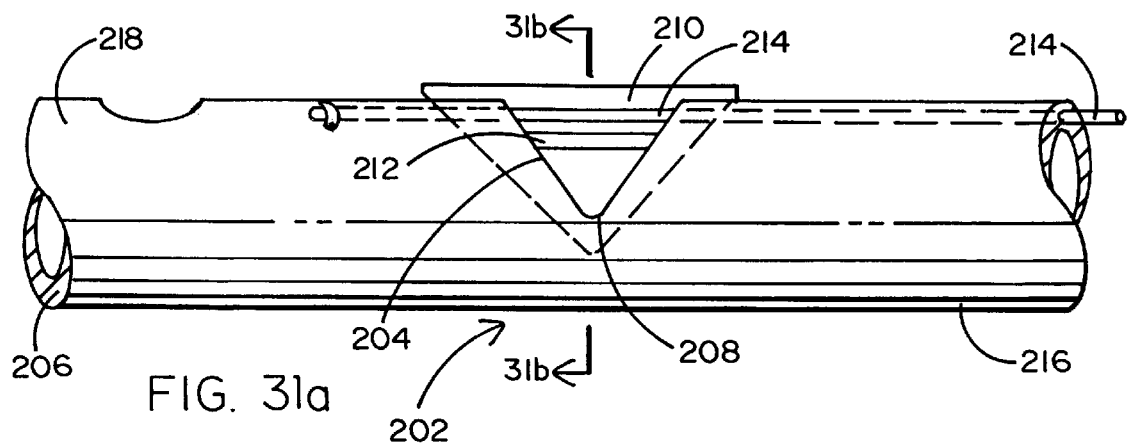
FIG. 31A is a side elevational view of an endotracheal tube with the inflatable cuff of FIG. 1 replaced by membranes.
Figure 31B:
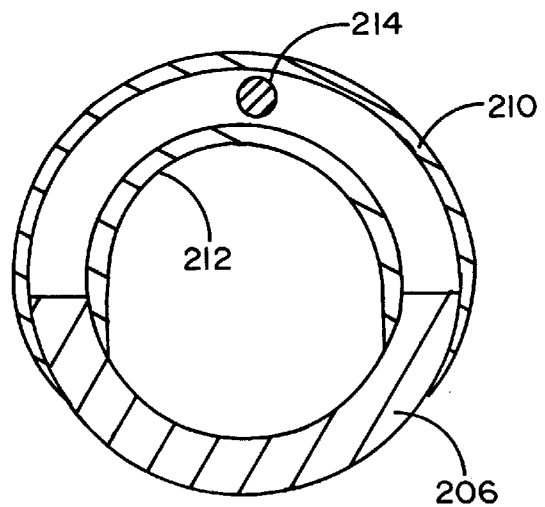
FIG. 31B is a vertical cross-sectional view of the endotracheal tube taken along the line 31B—31B of FIG. 31A.
Figure 32:
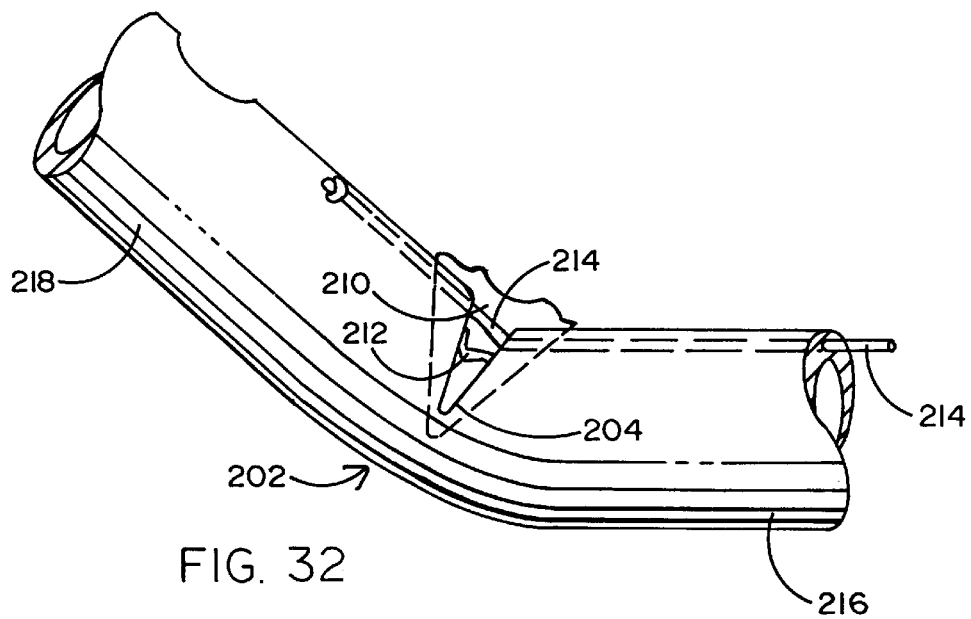
FIG. 32 is a side elevational view of the endotracheal tube of FIG. 31A with the cable pulled back to create a bend in the tube.

FIGS. 31a, 31b and 32 show a further embodiment in which one or two membranes are used rather than the inflatable cuff as described above. In this embodiment, a flexible portion 202 of the tube is created by providing one or more notches 204 in a wall 206 with a bottom 208 of the notch functioning as a hinge. An outer membrane 210 covers the notch 204. An inner membrane 212 may be placed inside the tube in which case a cable 214 of the pulling mechanism is located between the outer membrane 210 and the inner membrane 212. The outer membrane 210 protects the walls of the body passage into which the tube is inserted from coming into contact with the cable. The outer membrane 210 can be sealed to the outer surface of the tube forming a fluid-tight seal. Alternatively or additionally, the inner membrane 212 can be sealed to the inner surface of the tube to form a fluid-tight seal.

Figure 34:
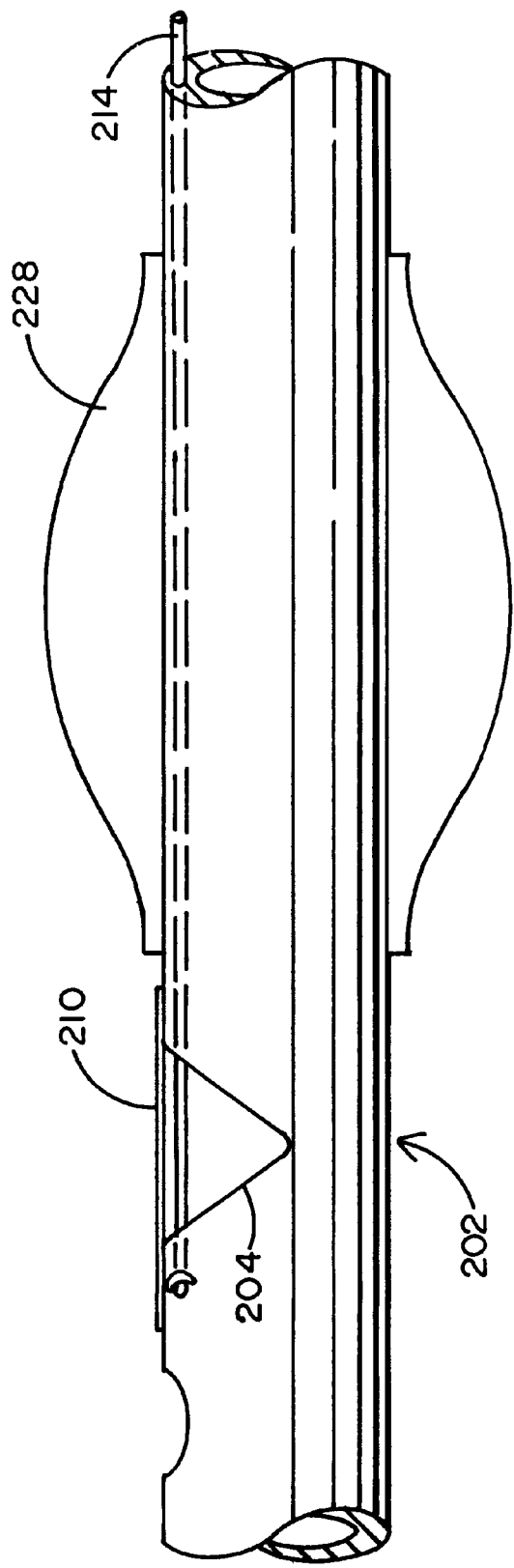
FIG. 34 is a side elevational view of an endotracheal tube having a notch disposed distally of the cuff.

FIG. 32 shows the cable 214 creating a temporary bend in the flexible portion of the tube covered by the membrane. The cable 214 extends from the proximal end 216 of the tube through a proximal end of the portion of the tube covered by the membrane, extending between the flexible portion 202 and the outer membrane 210. The distal end of the cable 214 is attached to the wall 206 distal to the notch 204. The cable 214 can be attached to the wall 206, for example, at a position distal to (as illustrated in FIG. 31a) or below (as illustrated in FIG. 34) the outer membrane 210. A pulling force is applied to the proximal end of the cable 214 at the proximal end 216 of the tube.

As explained above with respect to other embodiments, the flexible portion 202 of the tube need not include a notch, but can formed in other ways. For example, the tube can be formed from a polymeric material with the portion of the tube forming the flexible portion 202 being a polymer of different chemical properties having a greater flexibility than surrounding portions of the tube. Also, the flexible portion 202 can be heat, ultrasound or UV radiation treated to create flexibility greater than surrounding portions of the tube.

While this embodiment does not show the use of a spring, a spring can be used within the tube for the same purposes as set forth in other embodiments.

As shown in FIG. 34, an inflatable cuff 228 can be used with the embodiment of FIG. 31a. Thus, the flexible portion of the tube 202 need not be within the inflatable cuff 228. The inflatable cuff 228 can be positioned proximate to the flexible portion 202 (as illustrated FIG. 34), can be positioned distal to the flexible portion 202, or can surround the flexible portion 202 (as illustrated in FIG. 8).

Figure 33:
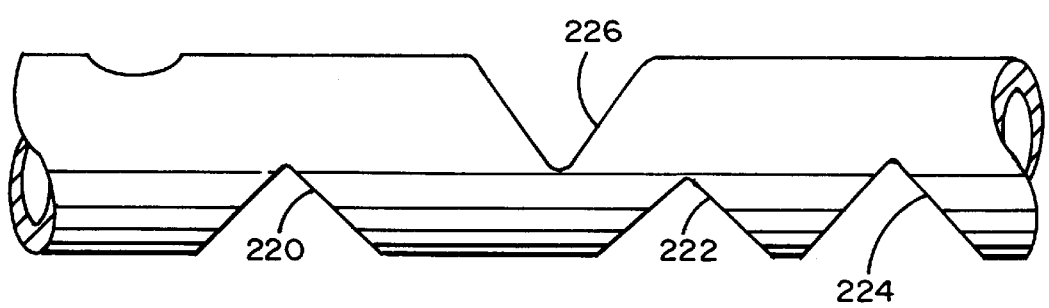
FIG. 33 is a side elevational view showing an embodiment of the invention utilizing multiple notches.

FIG. 33 shows flexible portions created by a plurality of notches 220–226. FIG. 33 shows the notch 226 oriented 180 degrees from the notches 220, 222, 224 relative to the axis of the tube. This allows bending of the tube in directions within a plane. Additionally, the notches can be oriented anywhere 360 degrees around the axis of the tube allowing the bending of the tube in directions outside of the plane. The multiple notches can be controlled by multiple cables oriented similarly to those shown in FIGS. 19, 19a, 20 and 20a. Each notch can have a cable that exits through the wall at the proximal end of the notch which then attaches to the wall just distal of the notch. As explained above with respect to other embodiments, the flexible portion of the tube need not include a notch, but can formed in other ways.

In the embodiments of the present invention described above and shown in the figures, some of the mechanisms for bending the primary tubular body, including the cables and the small diameter air/fluid supplying tubes, are shown extending within the walls of the primary tubular body from the proximate end of the body to the flexible region. Other of the mechanisms for bending the body are shown co-extruded to the exteriors of the primary tubular bodies. However, it is also intended that in all the described embodiments the mechanisms for bending the tubular body can extend within the walls of the body and/or can be co-extruded to the exterior and/or interior of the primary tubular body.

It is believed that the operation and construction of the present invention will be apparent from the foregoing description and, while the invention shown and described herein has been characterized as particular embodiments, changes and modifications may be made therein without departing from the spirit and scope of the invention as defined in the following claims.

We claim:

1. An apparatus for rapid intubation of the trachea, comprising:
   a hollow tube forming a distal end configured for insertion into the trachea and an opposite proximal end;

a flexible portion of the tube more flexible than surrounding portions of the tube, the flexible portion near the distal end of the tube;

a membrane attached to the tube covering the flexible portion to separate the flexible portion from the trachea;

a pulling mechanism extending from the proximal end of the tube and extending between the flexible portion and the membrane to attach near the distal end of the tube; and whereby application of a pulling force to the pulling mechanism from the proximal end of the tube causes the flexible portion to bend.

2. The apparatus of claim 1, further comprising additional flexible portions of the tube spaced apart from each other and covered by additional membranes wherein additional pulling mechanisms extend between the additional flexible portions and the additional membranes.

3. The apparatus of claim 2, wherein the pulling mechanism comprises multiple cables for bending the tube at the additional flexible portions.

4. The apparatus of claim 1, further comprising:

a wall of the tube having outer and inner surfaces and a passageway in the wall through which the pulling mechanism extends from the proximal end of the tube to a proximal end of the flexible portion;

an exit point formed in the tube near the proximal end of the flexible portion through which the pulling mechanism exits from the wall to extend between the flexible portion and the membrane; and an attachment point near the distal end of the tube at which the pulling mechanism is attached.

5. The apparatus of claim 4, wherein:

the membrane is attached to the outer surface and further comprising an inner membrane attached to the inner surface forming a fluid tight seal between the inner membrane and the inner surface.

6. The apparatus of claim 1, wherein the flexible portion has material removed therefrom.

7. The apparatus of claim 6, wherein the material is removed to create a hinged section in a portion of the tube opposite the portion of the tube covered by the membrane.

8. The apparatus of claim 7, wherein the removal of the material forms a notch passing from an outer surface of the tube into a lumen of the tube.

9. The apparatus of claim 1, wherein the flexible portion has a coiled spring enclosed therein.

10. The apparatus of claim 1, wherein the flexible portion is formed from a coiled spring located within the flexible portion of the tube and a circumferential portion of the wall of the tube surrounding the coiled spring is removed.

11. The apparatus of claim 1, wherein the flexible portion includes a structure having a corrugated tube surface structure that renders that portion more flexible than other portions of the tube.

12. The apparatus of claim 1, wherein the tube is formed from a polymeric material, the portion of the tube covered by the membrane being a polymer of different chemical properties having a greater flexibility than surrounding portions of the tube.

13. The apparatus of claim 1, wherein the tube is formed from a polymeric material, the flexible portion comprising a heat, ultrasound or UV radiation treated polymer of flexibility greater than surrounding portions of the tube.

14. The apparatus of claim 1, wherein the pulling mechanism comprises at least one cable.

15. The apparatus of claim 14, wherein the pulling mechanism includes a finger actuated trigger mounted to the proximal end of the tube, said finger actuated trigger being moveable proximally to place tension on the at least one cable causing the tube to bend in the desired region of the tube.

16. The apparatus of claim 15, further including a latch for temporarily maintaining the tension on the at least one cable until purposely released by an operator.

17. The apparatus of claim 14, wherein the at least one cable extends through an elongated space within a wall of the tube.

18. The apparatus of claim 14, wherein the at least one cable extends through the lumen of the tube.

19. The apparatus of claim 14, wherein the at least one cable is formed from a material selected from the group consisting of stainless steel wire, plastic filament and braided filament material.

20. The apparatus of claim 1, further comprising a plurality of cables for bending the flexible portion in at least two directions along at least one axis.

21. The apparatus of claim 1 wherein the pulling mechanism comprises a relatively stiff, longitudinally extending member.

22. The apparatus of claim 21 wherein the longitudinally extending member is disposed within a longitudinally extending channel formed in an outer wall of the tube.

23. An apparatus for insertion into a body, comprising:

a hollow tube forming a distal end configured for insertion into the body and an opposite proximal end;

a flexible portion of the tube more flexible than surrounding portions of the tube, the flexible portion near the distal end of the tube;

a membrane attached to the tube covering the flexible portion to separate the flexible portion from the body;

a pulling mechanism extending from the proximal end of the tube and extending between the flexible portion and the membrane to attach near the distal end of the tube; and whereby application of a pulling force to the pulling mechanism from the proximal end of the tube causes the flexible portion to bend.

24. An apparatus for insertion into a body, comprising:

a flexible structure formed from a wall having an outer wall surface, the flexible structure having a distal end configured for insertion into the body and an opposite proximal end;

a notch formed in the wall;

a membrane attached to the outer wall surface of the structure and covering the notch;

a pulling mechanism for creating a temporary bend in the structure at the notch, the pulling mechanism extending from the proximal end of the structure and passing from a proximal end of the notch into a region formed by the notch and the membrane; and a connection point near a distal end of notch to which a distal end of the pulling mechanism attaches so that application of a pulling force to a proximal end of the pulling mechanism causes the flexible structure to bend at the notch.

25. The apparatus of claim 24, further comprising additional notches covered by additional membranes, each having a pulling mechanism for bending the structure in at least two directions along at least one axis.

26. An apparatus for rapid intubation of the trachea, comprising:

a flexible structure formed from a wall having an outer wall surface, the flexible structure having a distal end configured for insertion into the trachea and an opposite proximal end;

a notch formed in the wall;

a membrane attached to the outer wall surface of the structure and covering the notch;

a pulling mechanism for creating a temporary bend in the structure at the notch, the pulling mechanism extending from the proximal end of the structure and passing from a proximal end of the notch into a region formed by the notch and the membrane; and a connection point near a distal end of notch to which a distal end of the pulling mechanism attaches so that application of a pulling force to a proximal end of the pulling mechanism causes the flexible structure to bend at the notch.

27. An apparatus for rapid intubation of the trachea, comprising:

a hollow tube forming a distal end configured for insertion into the trachea and an opposite proximal end;

a plurality of flexible portions of the tube more flexible than surrounding portions of the tube;

a plurality of actuating mechanisms for creating temporary bends in the flexible portions, the actuating mechanisms extending from the proximal end of the tube to the flexible portions, the actuating mechanisms actuated at the proximal end to temporarily bend the hollow tube; and a plurality of membranes covering the plurality of flexible portions to separate the actuating mechanism from the trachea.

28. The apparatus of claim 27, wherein the actuating mechanisms comprise at least one cable.

29. The apparatus of claim 27, wherein the flexible portions have material removed therefrom.

30. The apparatus of claim 29, wherein the material is removed to create a hinged section in the tube.

31. The apparatus of claim 27, wherein the flexible portions have coiled springs enclosed therein.

32. The apparatus of claim 27, wherein the flexible portions are formed from coiled springs located within the flexible portions of the tube and a circumferential portion of the wall of the tube surrounding the coiled spring is removed.

33. The apparatus of claim 27, wherein the tube is formed from a polymeric material, the flexible portion comprising a heat, ultrasound or UV radiation treated polymer or a polymer of different chemical properties than the surrounding portions of the tube having flexibility greater than the surrounding portions of the tube.

34. An apparatus for rapid intubation of the trachea, comprising:

a hollow tube having a distal end configured for insertion into the trachea and an opposite proximal end;

an inflatable cuff attached to an outer surface of the hollow tube between the distal end and the proximal end of the tube; and an expandable chamber for creating a temporary bend in a desired region proximate the distal end of tube, the expandable chamber being adapted to receive fluid under pressure;

whereby introduction of fluid under pressure into the expandable chamber causes the tube to bend in the desired region.

35. The apparatus of claim 34, wherein the desired region is the outer surface of the tube covered by the cuff.

36. The apparatus of claim 35, wherein the cuff covers a portion of the tube having material removed therefrom, rendering that portion more flexible than the remainder of the tube.

37. The apparatus of claim 36, wherein the portion of the wall of the tube covered by the cuff is removed to create a hinged section.

38. The apparatus of claim 35, wherein said structure is a bellows section along the outer surface of the tube.

39. The apparatus of claim 35, wherein the desired region includes structure that renders that portion more flexible than other portions of the tube.

40. The apparatus of claim 39, wherein the tube is formed from a polymeric material, the portion of the tube covered by the cuff being a polymer of different chemical properties having a greater flexibility then the remainder of the tube.

41. The apparatus of claim 39, wherein the tube is formed from a polymeric material, the portion of the tube covered by the cuff comprising a heat, ultrasound or UV radiation treated polymer of flexibility greater than the remainder of the tube.

* * * * *